US008554518B1

(12) United States Patent
Claps

(10) Patent No.: US 8,554,518 B1
(45) Date of Patent: Oct. 8, 2013

(54) DISCRETE PRINCIPAL COMPONENT ANALYSIS (DPCA) FOR PATTERN RECOGNITION AND DIAGNOSTICS OF TISSUE PATHOLOGIES SUCH AS CANCER

(76) Inventor: Ricardo Claps, San Jose, CA (US)

( * ) Notice: Subject to any disclaimer, the term of this patent is extended or adjusted under 35 U.S.C. 154(b) by 607 days.

(21) Appl. No.: 12/726,427

(22) Filed: Mar. 18, 2010

Related U.S. Application Data

(63) Continuation-in-part of application No. 11/767,458, filed on Jun. 22, 2007, now Pat. No. 7,783,458.

(51) Int. Cl.
*H03F 1/26* (2006.01)
*H04B 15/00* (2006.01)

(52) U.S. Cl.
USPC ........................................................ 702/189

(58) Field of Classification Search
USPC .............................................................. 702/189
See application file for complete search history.

(56) References Cited

U.S. PATENT DOCUMENTS

| 7,439,739 | B2 * | 10/2008 | Beatty ............................ 324/309 |
| 2002/0053545 | A1 | 5/2002 | Greef |
| 2007/0038041 | A1 | 2/2007 | Yang |
| 2011/0286648 | A1 * | 11/2011 | Sharif et al. .................. 382/131 |

OTHER PUBLICATIONS

I. Lerche ; "Some Notes on Entropy Measures," Mathematical Geology, vol. 19, No. 8, 1987.
C.E. Shannon; "A Mathematical Theory of Communication," The Bell System Technical Journal, vol. 27, pp. 379-423, 623-656, Jul.-Oct. 1948.
NIH-National Cancer Institute; "What you need to know about Melanoma," NIH Publication No. 02-1563, Revised Jul. 2002, Printed Sep. 2002.
Hughes Talbot et al; "An overview of the Polartechnics SolarScan melanoma diagnosis algorithms;" CSIRO-Mathematical and Information Sciences. http://citeseerx.ist.psu.edu/viewdoc/download?doi=10.1.1.10.3460&rep=rep1&type=pdf, 2003.
NIH-National Cancer Institute; "What you need to know about Skin Cancer," NIH Publication No. 05-1564, Revised Jun. 2005, Printed Sep. 2005.

* cited by examiner

*Primary Examiner* — Aditya Bhat

(57) ABSTRACT

A method for recognizing figures in an image frame provided by an optical device is disclosed. The method includes selecting a set of calibration images having characteristic figures; selecting a number of horizontal and vertical channels for dividing the image, obtaining a digital signature for the image corresponding to each channel to create a calibration image matrix, obtaining a first set of characteristics and a second set of characteristics from said calibration image matrix and selecting two coordinates from at least one component in each of said first and second sets of characteristics from said calibration image matrix; forming a pattern vector from said selected coordinates from at least one component in each of said first and second sets of characteristics from said calibration image matrix, forming a calibration pattern matrix using pattern vectors from a plurality of said calibration images, forming a sample pattern vector from said selected coordinates from at least one component in each of said first and second sets of characteristics from a sample image, obtaining a two-dimensional projection of the vector resulting from transforming a sample pattern vector by the calibration pattern matrix, and determining whether the sample figure corresponds to a calibration pattern by the location in a two-dimensional plot of said projection. A method for recognizing tissue conditions in a sample tissue image frame provided by an optical device using the pattern recognition as described above is also provided.

20 Claims, 17 Drawing Sheets

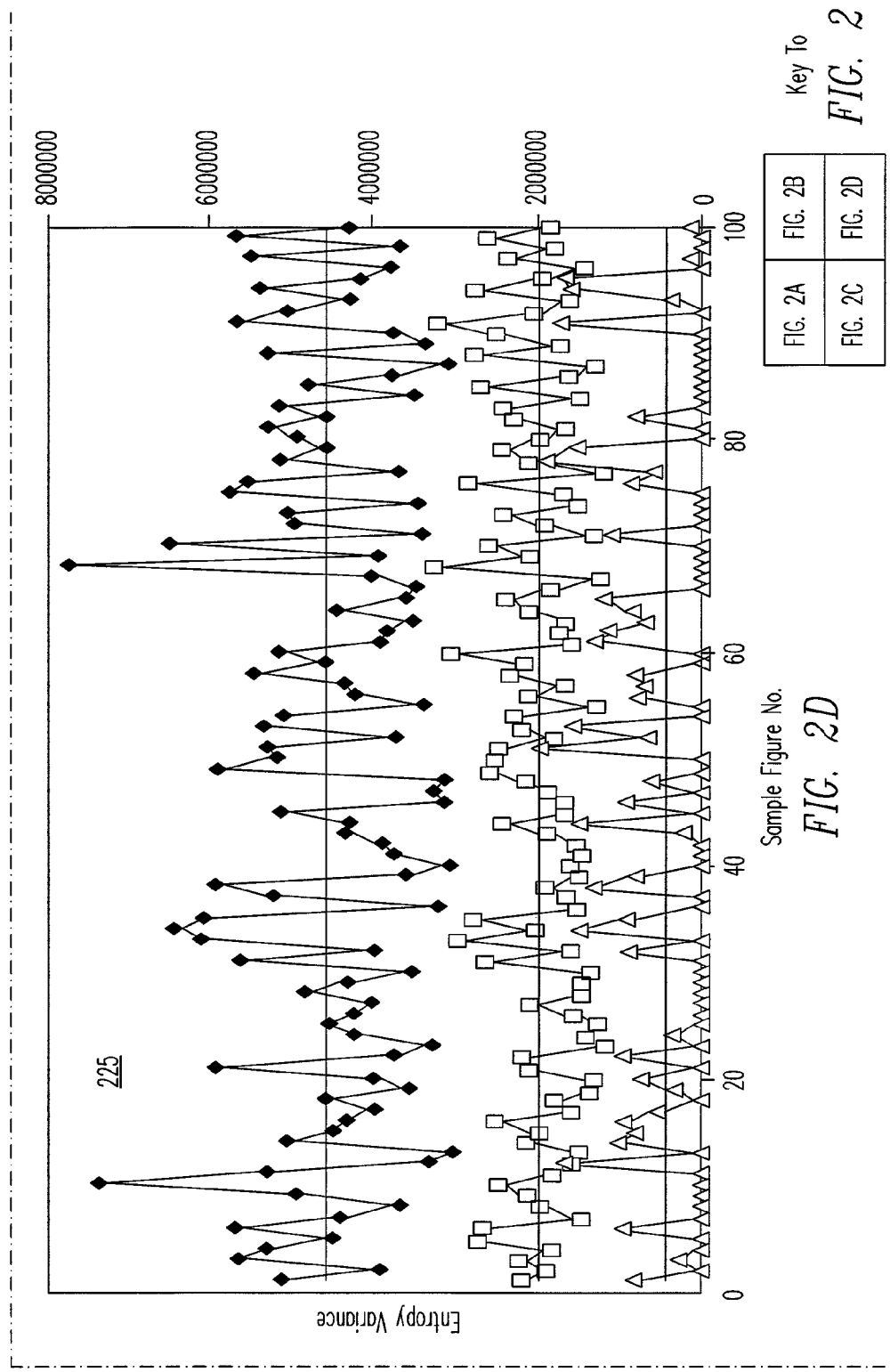

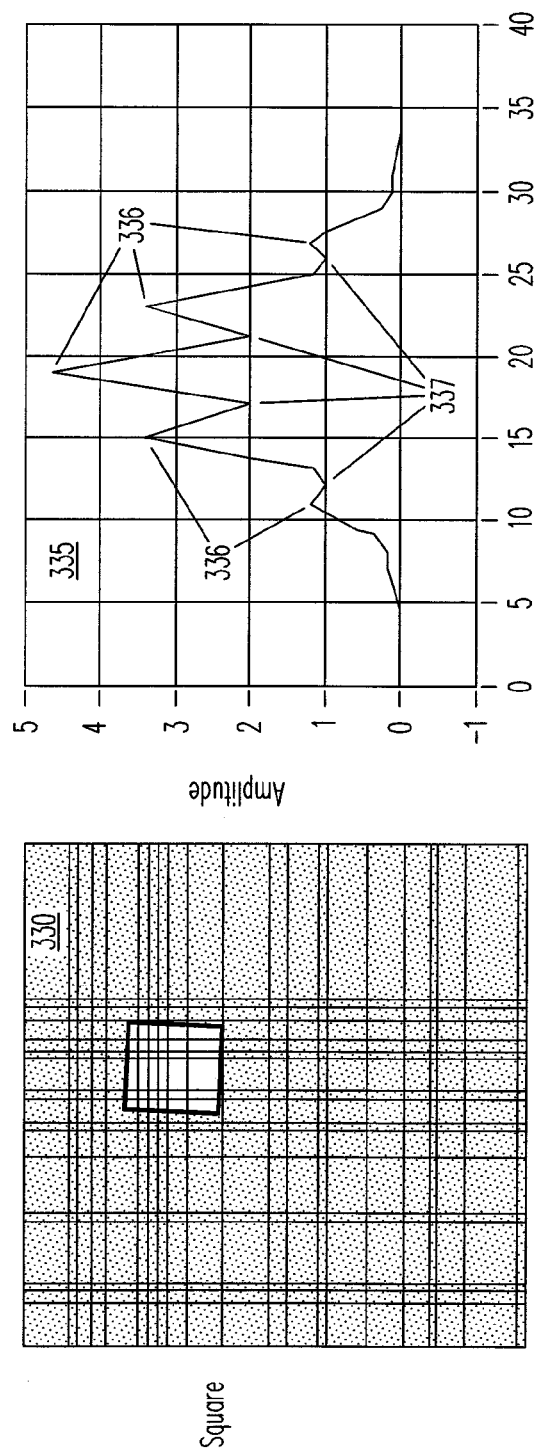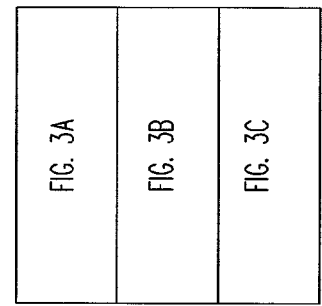
FIG. 3C
Key To
FIG. 3

Key to

Key To FIG. 5

DISCRETE PRINCIPAL COMPONENT ANALYSIS (DPCA) FOR PATTERN RECOGNITION AND DIAGNOSTICS OF TISSUE PATHOLOGIES SUCH AS CANCER

CROSS-REFERENCE TO RELATED APPLICATIONS

The present application is a continuation in part of U.S. patent application Ser. No. 11/767,458 filed on Jun. 22, 2007, now U.S. Pat. No. 7,783,458, the content of which is incorporated herein by reference in its entirety.

The following disclosure is related to U.S. patent application Ser. No. 12/551,404, filed on Aug. 31, 2009, now U.S. Pat. No. 7,944,555, incorporated herein by reference in its entirety, and also is related to co-pending U.S. patent application Ser. No. 12/697,227, filed on Jan. 30, 2010, incorporated herein by reference in its entirety.

FIELD OF INVENTION

This invention relates to structures and methods for implementing the technique of Principal Component Analysis using an algorithm called Discrete Principal Component Analysis in a reduced parameter space with high computational efficiency. More particularly, this invention makes it possible to implement the technique using simple and low-cost hardware both in the sensor and the transducer components(for example, using hardware such as photo-detector arrays, camera arrays and similar detectors).

BACKGROUND

The measurement of the characteristics of complex systems is a technological challenge particularly if the measurements must be carried out in real time as opposed to a laboratory environment. Usually complex systems, such as compounds containing many constituents, or highly detailed tissue images must be analyzed in a laboratory using sensitive and expensive equipment. In some cases, the analysis of tissue images is performed by a qualified and experienced pathologist, who can identify features or patterns in the image that even an unskilled person is unable to detect. As a result, with measurement systems of the type used in laboratories, it is not possible to determine in real time the constituents of materials or compounds outside of the laboratory, or the nature of certain portion of tissue being sampled in the surgical room. Moreover, prior art systems such as a typical grating-based spectrometer, utilize a large number of channels, such as 256, 512 or 1024 channels. This makes the prior art instruments expensive and requires the use of high-end computation equipment to process the data.

What is needed is a fast and cost effective system which allows one to determine the constituents of materials or compounds, for example, outside of the laboratory. Further, it is recognized the need for a reliable pattern recognition system that can provide tissue diagnostics in vivo, in real time.

SUMMARY

A method for recognizing patterns and figures in an image frame provided by an optical device is presented. The method includes selecting a calibration set of images having characteristic figures; selecting a number of horizontal and vertical channels for dividing the image; obtaining a digital signature for the image corresponding to each channel to create a calibration image matrix; obtaining a first set of characteristics and a second set of characteristics from said calibration image matrix; selecting two coordinates from at least one component in each of said first and second sets of characteristics from said calibration image matrix; forming a pattern vector from said selected coordinates from at least one component in each of said first and second sets of characteristics from said calibration image matrix; forming a calibration pattern matrix using pattern vectors from a plurality of said calibration images; forming a sample pattern vector from said selected coordinates from at least one component in each of said first and second sets of characteristics from a sample image; selecting a test vector from a set of vectors obtained by multiplying a sample pattern vector by each of the calibration image matrices; and determining whether the sample figure corresponds to a calibration pattern by the location in a two-dimensional plot of a two-dimensional projection of said test vector.

A method for recognizing tissue conditions in a sample tissue image frame provided by an optical device, is also provided. The method includes the steps of selecting a calibration set of tissue images having characteristic tissue conditions; selecting a number of horizontal and vertical channels for dividing the tissue image; obtaining a digital signature for the tissue image corresponding to each channel to create a calibration tissue image matrix; obtaining a first set of characteristics and a second set of characteristics from said calibration tissue image matrix; selecting two coordinates from at least one component in each of said first and second sets of characteristics from said calibration tissue image matrix; forming a pattern vector from said selected coordinates from at least one component in each of said first and second sets of characteristics from said calibration tissue image matrix; forming a calibration pattern matrix using pattern vectors from a plurality of said calibration tissue images; forming a sample pattern vector from said selected coordinates from at least one component in each of said first and second sets of characteristics from a sample tissue image obtained from a sample tissue; obtaining a two-dimensional projection of the vector resulting from transforming a sample pattern vector by the calibration pattern matrix; determining whether the sample tissue corresponds to a characteristic tissue condition in the calibration tissue pattern by the location in a two-dimensional plot of said projection.

Embodiments of this invention will be more fully understood in view of the following detailed description taken together with the following drawings.

DESCRIPTION OF THE DRAWINGS

FIG. 2D. Shows the processing of the images using an entropy variance calculation according to some embodiments of the present invention.

FIG. 3C. Shows a trace of an auto-correlation of an image vector according to some exemplary embodiments of the present invention, using a square.

DETAILED DESCRIPTION

Figure 1A:
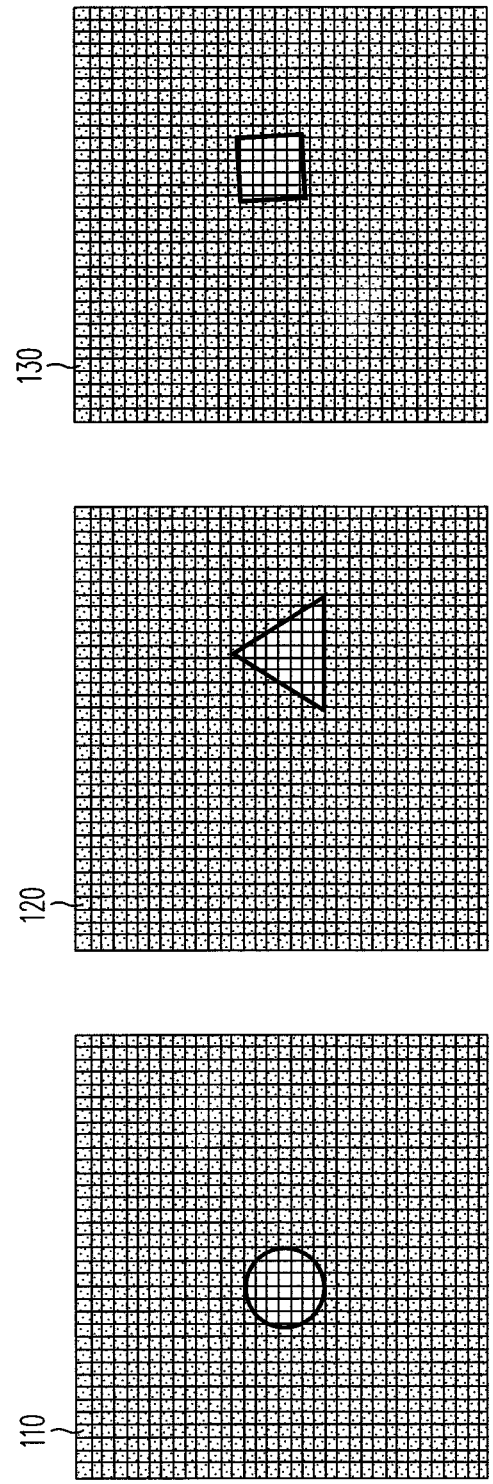
FIG. 1A. Shows the dividing of the image field in some exemplary embodiments of the present invention.

In accordance with this invention, the constituents of complex systems are measured by optical means, in a fast, cost efficient manner. By "complex systems" is meant systems with multiple components to be measured, either in a chemical sense, in a geometric sense, in a physiological sense, or in any combination of these. The optical means of measurement may be spectroscopic (separating light by wavelength), interferometric (separating light by phase), intensity-based, imaging-based, or any combination. The speed and simplicity of measurement associated with systems operating in accordance with this invention means that this invention can be used in a broad variety of field applications or in applications where the details of the measurement procedure provide new information on a given phenomenon.

The structures and methods of this invention allow one to achieve a significant reduction in the cost of measuring the constituents of complex systems while simultaneously decreasing the time required to make these measurements. The following description is illustrative only. Other embodiments of this invention will be obvious in view of this disclosure.

In general, a set of n measurements performed on m different samples can be organized in the form of an n×m matrix, P. Principal Component Analysis (PCA) is a mathematical algorithm that makes use of basic linear algebra operations in order to rewrite any given n×m matrix, P, in the form:

$$P = C \cdot R \quad (1)$$

In equation (1), C is an n×r matrix, representing the calibration of the system with known values of the principal components, and R is an r×m matrix, representing the unknown composition of the said principal components in the sample being measured. For example, in one embodiment of this invention, matrix C can be associated with a general set of properties of the measurement strategy, i.e. a quality of the measurement that remains constant from one measurement to the next, and matrix R can be associated with a specific property of the sample being analyzed. For example, a sample could be a solution containing a number of constituents. In one embodiment, each constituent is a principal component. For example, if the sample is blood, the constituents (i.e. the principal components) could include red blood cells, white blood cells, glucose and cholesterol among others. The elements of matrix R are the actual properties of the sample that need to be determined by the measurement. For purely practical reasons, matrix R will be referred to as the "concentrations" matrix. In some applications of this technique, the values of this matrix may refer to the specific concentrations of the different constituents (sometimes also called "analytes") in a given sample. In other applications, the values of the numbers in the concentration matrix, R, may refer to the probability or likelihood for a given image to be a representation of a known object. The r columns of matrix C are called "loading vectors" and correspond to the "Principal Components" of the measurement configuration. Equation (1) establishes that a linear relation may exist between the "concentrations" in the experiment, R, and the measurement results, P.

Once matrix C is determined, then solving Eq. (1) for R is straightforward, as in:

$$R = (C^T \cdot C)^{-1} \cdot C^T \cdot P \quad (2)$$

In Eq. (2), it is assumed that the matrix, $$\xi \equiv (C^T \cdot C),$$

is non-singular (otherwise, the matrix C is ill-defined and the measurement strategy needs revision). Note that the procedure described by Eqs. (1) and (2) is quite general and involves a measurement that can be as detailed as desired, since matrices P (measurement) and R are two-dimensional arrays of data. Matrix C is formed by previous knowledge of the experimental conditions in which the measurement will be carried out. This procedure could imply, but is not limited to, using a given number of sampling measurements or calibrations, with known concentrations, $\tilde{R}$. Labeling the calibration concentrations and calibration measurements as $\tilde{R}$ and $\tilde{P}$, respectively, we can find C, from Eq. (1), as $$C = \tilde{P} \cdot \tilde{R}^t (\tilde{R} \cdot \tilde{R}^t)^{-1} \quad (3)$$

The total number of operations, Z, required to solve Eqs. (1) and (2), is given by:

$$Z = r^3 + r^2 \cdot n + r \cdot n \cdot m \quad (4)$$

Equation (4) can be derived from the principles discussed in the book by Kevin R. Wadleigh and Isom L. Crawford entitled "Software Optimization for High-Performance Computing" published in May 18th, 2000, by Prentice Hall, ISBN-10: 0-13-017008-9. In equation (4), r is the number of principal components, that is, the number of constituents in the sample, and n is the number of individual measurements taken for each sample. For example, n could be the number of pixels in a photo-detector array, each pixel collecting light corresponding to a specific wavelength unique to that pixel, or a specific portion of the object being imaged. The number of measurements on the samples collected during the experiment is expressed by "m." Typically, this number will be one (1), since the analysis is performed only at one location at a given time. However, a more complex sensor architecture can be envisioned where measurements of different samples are taken simultaneously, or measurements of the same sample at different times are considered in the same analysis, in which case the number "m" may be much larger than 1.

It is seen that the complexity of the calculation routine increases dramatically as the number of principal components (also called "loading vectors"), r, grows. However, the variance of the results, $\sigma_{max}$, reduces at about the same rate, as a function of r. This results from the dependence of R on the matrix $\xi^{-1}$, shown in Eq. (2). Here, the variance of a multiple set of components will be defined as the square root of the sum of the variance squared for each of the components: $\sigma = \sqrt{\sigma_1^2 + ... + \sigma_k^2}$. FIG. 1 in patent application Ser. No. 11/767,458 illustrates the two competing effects, where the parameter $\sigma_{max}$ is proportional to the maximum possible determinant that can be found for a specific problem with a 3-component vector solution. On the other hand, of the three parameters, r, n, and m, in Eq. (4), typically the largest one is the dimension of the coordinate space, n. This may also be the parameter that is most costly from the hardware point of view. Each of the entries in this space is a data point collected by some photo-sensitive device, either a pixel in a CCD or CMOS detector array, or a photodetector coupled to an electrical step-scanner of some sort.

In accordance with the present invention, PCA techniques are used with a parameter space, n, substantially reduced by one or more orders of magnitude. Sometimes the parameter space is referred to by its "dimensionality", i.e. the number of channels n, which may correspond to the number of individual measurements taken for one sample (provided the sample is run through the hardware which does the measurements only once). This will not only reduce the number of operations needed to perform any given calculation, but also substantially reduce the costs and complexity of measurement strategies. Here, and for the rest of this disclosure, the term "precision" is a function of the variance in the measurement. The larger the variance, the poorer the precision of the measurement. There is, however, a limit to the degree of reduction in the number, n, of measurement channels to be used by the measurement system. This limit is given by the concept of Entropy Variance, which will be discussed below.

Discretization Technique

Mathematically, the process of discretization is a summation of matrix components over a certain number, d, of elements. This is described in Eq. (5) below, $$\tilde{C}_{ik} = \sum_{j}^{d} \beta_i \cdot C_{(i \cdot d + j)k} \quad (5)$$

The factor $\beta_i$ is a parameter that may be adjusted in the process of optimization, also defined herein as training or calibration of the instrument in question. The dimensionality of the PCA problem is then reduced from n, to n'=n/d, therefore reducing the computational time and the hardware requirements concomitantly. However, an operation such as the one described in Eq. (5) carries the cost of information loss due to reduced precision. On the other hand, as the discretization process takes place, there is a reduction in 'graininess' that increases the information content of the reduced data set. The balance between these competing effects can be quantified in different ways; one useful procedure is through the relative entropy matrix (REM)[1]. A variable is defined that quantifies the information content of a given data set. This is called the 'entropy of the pooled data set'. In the case considered here (PCA analysis), the 'pooled' data set is matrix C. Note that matrix C is built by using selected data sets called principal components (cf. Eq. (3)). The numbers representing the magnitudes of the principal components in matrix C are known because the samples used to generate the values in matrix C have been carefully prepared with known magnitudes of the principal components. These samples with known magnitudes of principal components are then measured by the same hardware that will be used to measure the magnitudes of the principal components in samples with unknown magnitudes of the same principal components. Therefore, matrix C is directly linked to the hardware of the measurement technique. The entropy is defined as:

$$E_n(k) = -\frac{1}{\ln n} \sum_{j=1}^{n} C_{jk} \ln(C_{jk}) \quad (6)$$

[1] I. Lerche; "Some Notes on Entropy Measures", Mathematical Geology, Vol. 19, No. 8, 1987.

Where $C_{ij}$ are the components of matrix C and n is the number of rows of matrix C. The number of rows of matrix C may be the dimension of the coordinate space, according to some embodiments of the present invention.

By maximizing the entropy, $E_n$, the data set is guaranteed to carry the maximum possible information content[2]. Equation 6 actually refers to a "relative" entropy measure, assuming a maximum normalized value of $E_n(k)=1$. The parameter k is a counting index given by $1 \leq k \leq m$, and m is the total number of different records of data available, which in the case of matrix C would be the total number of principal components to be used, r.

[2] C. E. Shannon; "A Mathematical Theory of Communication", The Bell System Technical Journal, Vol. 27, pp. 379-423, 623-656, July, October, 1948.

A variance in the average relative entropy, or Entropy Variance, is then defined as:

$$\delta R(n)^2 = \frac{1}{m-1} \cdot \sum_{k=1}^{n} (E_n(k) - \langle E_n(k) \rangle_n)^2 \quad (7)$$

Entropy, $E_n$, is not the most convenient parameter to characterize the information content of a given data set. The parameter becomes indeterminate for extreme values of the data size, n, like, n=1, or n approaching infinity. A more convenient criterion, rather than to maximize the entropy, is the minimization of the Entropy Variance, $\delta R(n)$ (Eq. (7)), (Lerche, 1987).

Optimization/Training/Calibration

Once it has been established that a data discretization procedure renders more information and at a lower cost for a given problem, the next crucial step of the dPCA technique involves the selection of an optimized set, with a fixed number of discrete data subgroups.

Some embodiments of the dPCA systems and methods described in the present disclosure include image processing and pattern recognition systems and methods. For example, in one application the object of analysis constitutes a 2-dimensional field of points that form the pixilated image of a given object. This data set can be retrieved by any optical means, which may include, but is not limited to, a CCD/CMOS camera or a bundle of optical fibers attached to a scanner head. Also, the information stored in each pixel can have analog or digital format, and can be related to a multi-wavelength content, a state of polarization of light, the intensity of light, and/or the phase of an electromagnetic field. In this configuration, the role of the dPCA technique is to group together the pixel information, as in Eq. (5), and apply a "measure" operation to the reduced data set that allows for a simple identification of the objects contained in the field of view.

In the treatment of diseases such as cancer, and particularly in the treatment of melanoma and malignant melanoma, visual inspection of the suspect tissue is a paramount diagnostic tool, usually employed at the early stages of the disease. According to the document "What you Need to Know About Melanoma," published by the National Institutes of Health, National Cancer Institute, NIH Publication No. 02-1563, Revised July 2002, Printed September 2002, incorporated herein by reference in its entirety (hereinafter 'NIH-1563'), malignant melanoma may be identified by looking to four characteristic features in an image of the skin: Asymmetry (A), Border (B), Color (C), and Diameter (D). The four elements ABCD are related to geometrical patterns of a skin image that may be provided by an optical imaging device such as a laser scanner, or a video camera. Other optical devices that may be used to provide the skin image or a section thereof may be related to interferometric techniques, such as optical coherence tomography. According to some embodiments of the present invention, a pattern vector may be formed by using features such as A, B, C, and D, as described in relation to FIG. 8, below. Using a calibration set of images and image matrices generated from the pattern vectors having A, B, C, and D features as described in some embodiments of the present invention, a technique and procedure for the diagnostic of malignant melanoma is provided. Furthermore, a Color (C) component or feature of the skin image may be associated to a spectroscopic parameter, such as the wavelength of light.

FIG. 1A shows the division of an image frame according to some embodiments of the present invention. The number of horizontal sectors is the same as the number of vertical sectors for each of the images representing a circle 110, a triangle 120, and a square 130. Moreover, the dimensions of each of the segments are homogeneous for the entire image frame being subdivided. It is understood that the embodiments depicted in FIG. 1 a are exemplary only, and some embodiments may have a number of horizontal sectors that is different from the number of vertical sectors. Further, some embodiments of the present invention may include dividing an image frame in sectors that have different sizes across the image plane.

Figure 1B:
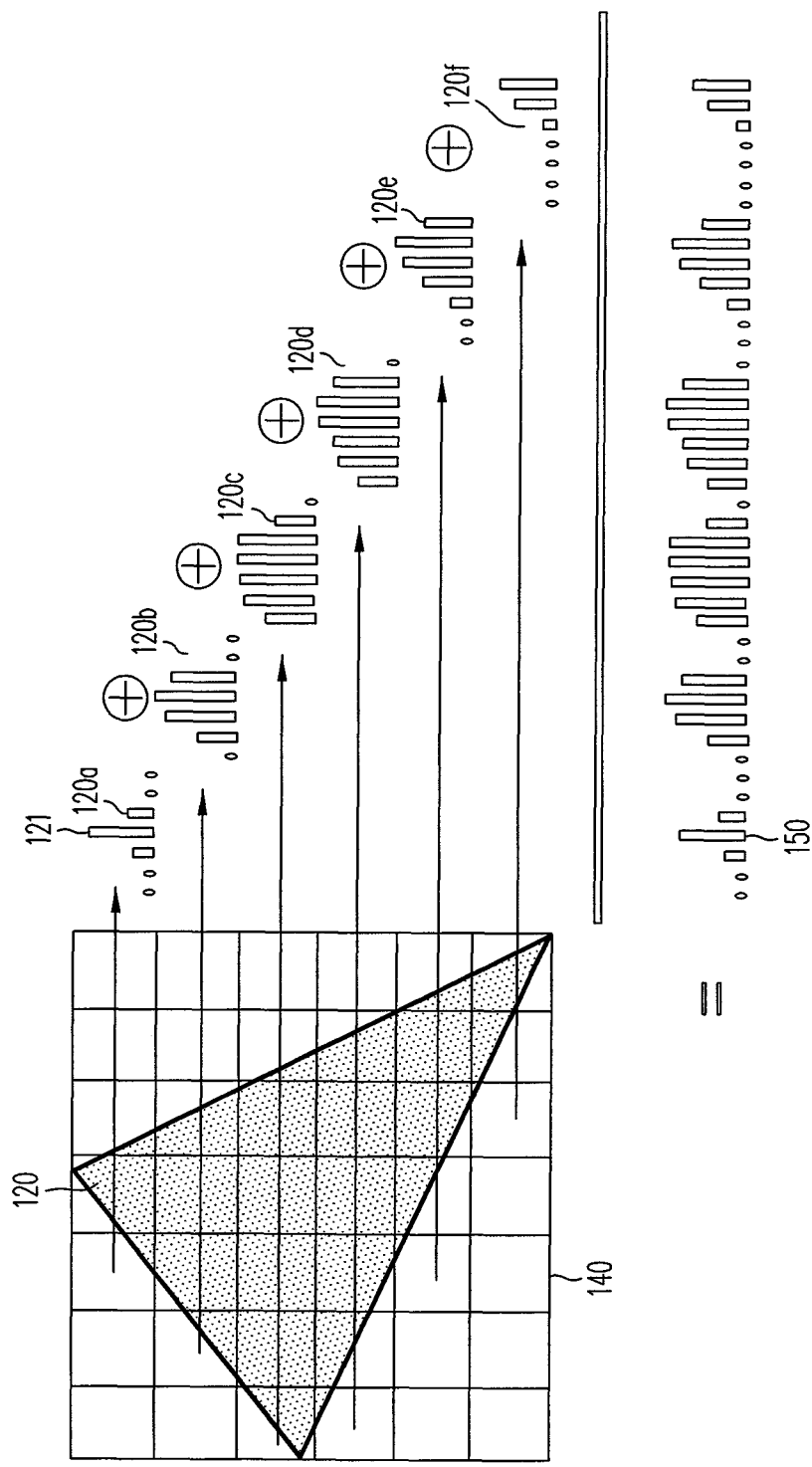
FIG. 1B. Shows the forming of a linear array or vector of digitized values from the divided image as in FIG. 1A, according to some embodiments of the present invention.

FIG. 1B shows the forming of a linear array or vector of digitized values from the divided image as in FIG. 1A, according to some embodiments of the present invention. A triangle 120 is used as an example in FIG. 1B, but other figures may be used in the same manner. For each of the 'pixels' or sectors in the divided image, a numeric value is given. Said numeric value associated with each 'pixel' or sector may be the sum of the color intensity of all the real pixels included within said 'pixel' or sector. A first step includes selecting the divisions in FIG. 1A that circumvent the element to be analyzed, triangle 120, to form a segment 140 such that on any row or column of segment 140 at least one 'pixel' 121 has a value different from zero. Figure segment 140 has 'u' rows of length 'v' each, where 'u' and 'v' are integers not necessarily equal to one another. The pixel rows 12a-120f are then joined together to form a one-dimensional array or vector 150, of dimension f=u×v.

According to some exemplary embodiments of the present invention, the identification of a single object within a 200× 200 pixel frame that has a neutral background (grey) is provided. It is understood that the number of pixels included in the image frame as collected by an optical device is not limited to 200, but it could be any other integer number. Nor is it necessary for the number of vertical pixels to be equal to the number of horizontal pixels. The objects in question are a circle, a triangle, and a square of the color, located at an arbitrary position within the frame, and in the case of the triangles and the squares, with an arbitrary orientation. The size of the figures may also be different, according to some embodiments of the present invention. The field of view is then subdivided into a number, n, of "pixels" on each axis (without loss of generality: $n_x = n_y = n$). For a given number of pixels in the image, $n^2$, a discriminator is defined as $$D_n = \frac{1}{n^2} \sum_i \left( \sum_j \tilde{C}_{ij} \cdot \ln(\tilde{C}_{ij}) \right)^2 \otimes \sum_j \left( \sum_i \tilde{C}_{ij} \cdot \ln(\tilde{C}_{ij}) \right)^2 \quad (8)$$

where the elements $\tilde{C}_{ij}$ are defined in Eq. (5).

Figure 2A:
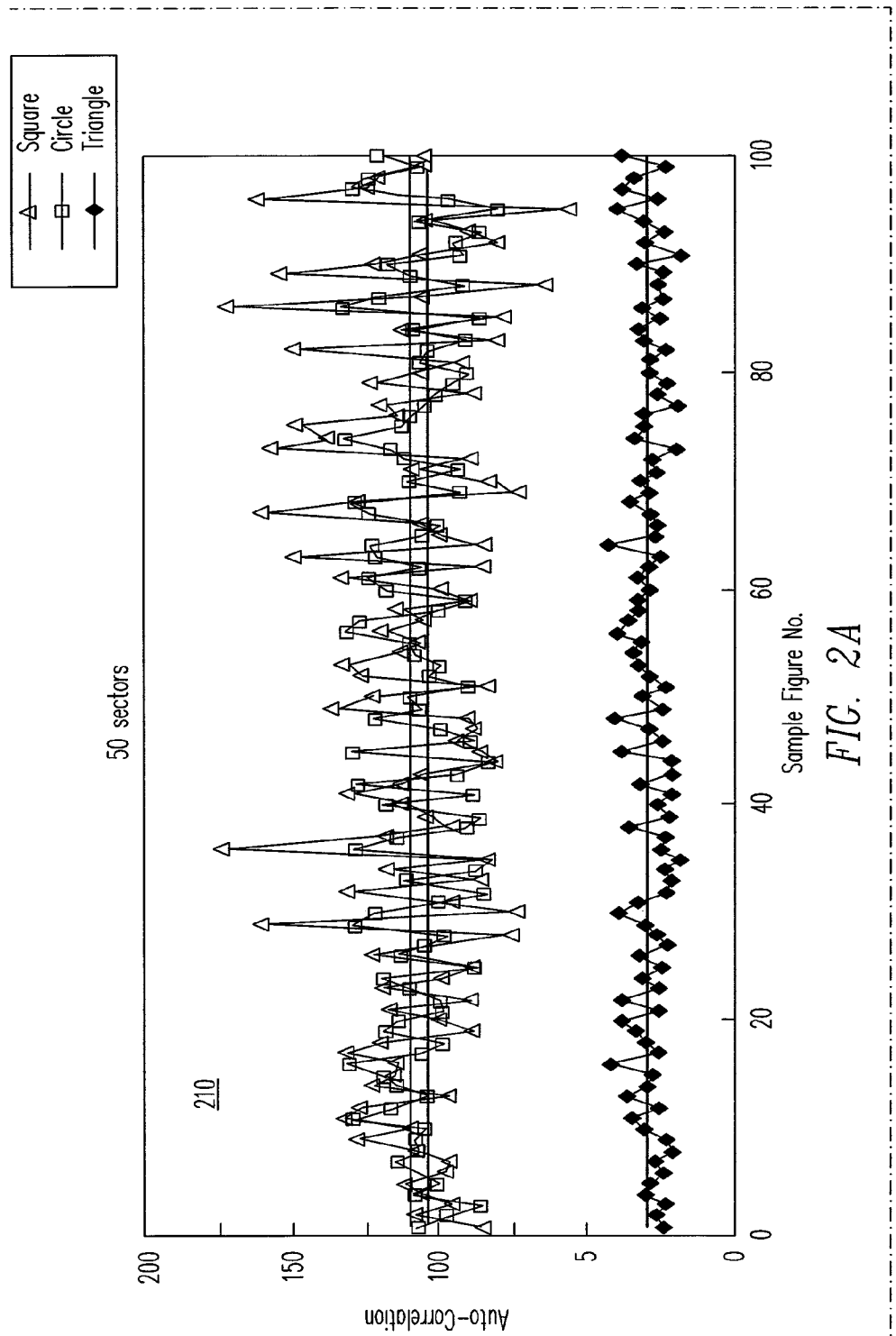
FIG. 2A. Shows the processing of the images using an auto-correlation calculation according to some embodiments of the present invention.
Figure 2B:
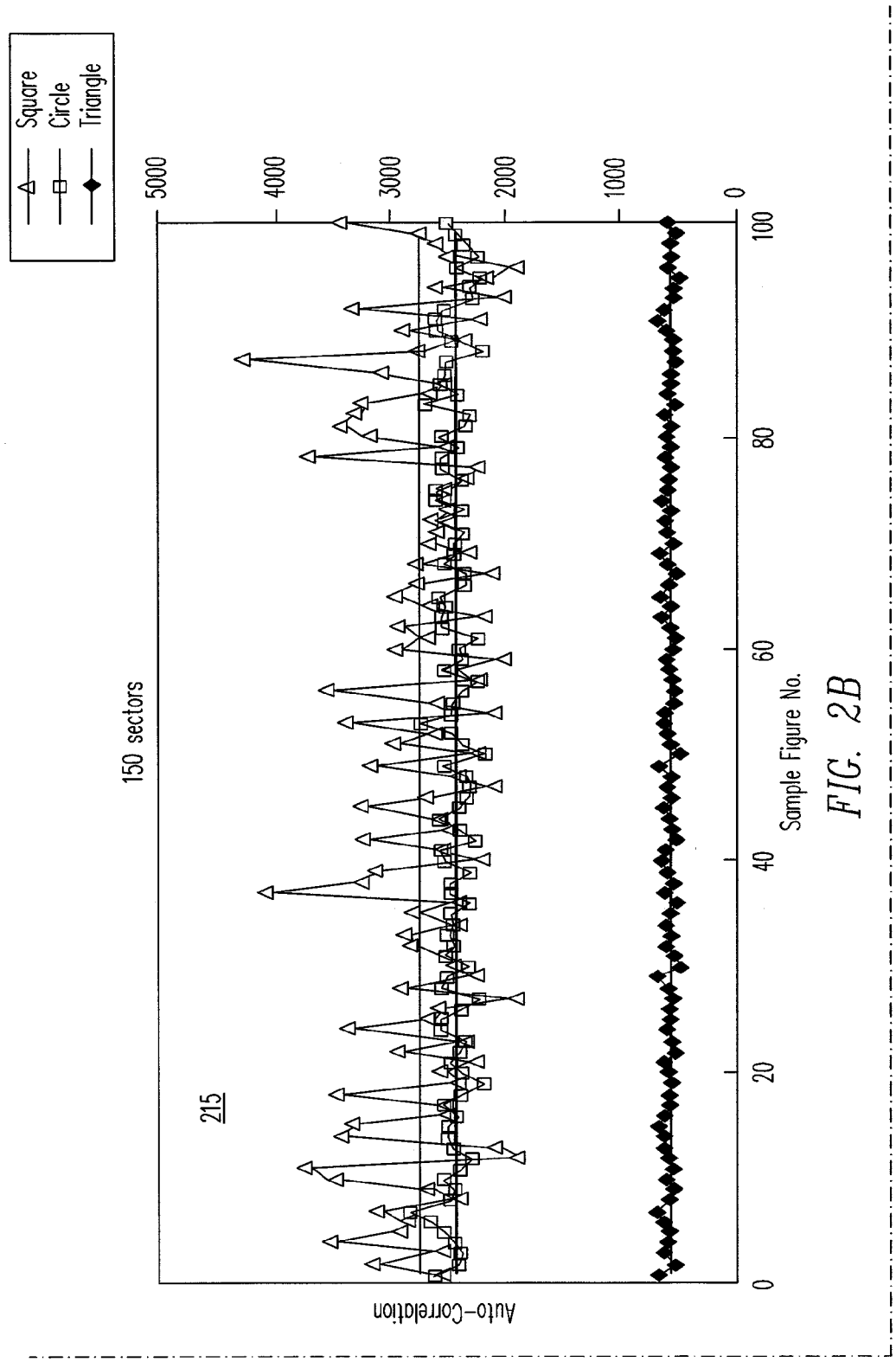
FIG. 2B. Shows the processing of the images using an auto-correlation calculation according to some embodiments of the present invention.
Figure 2C:
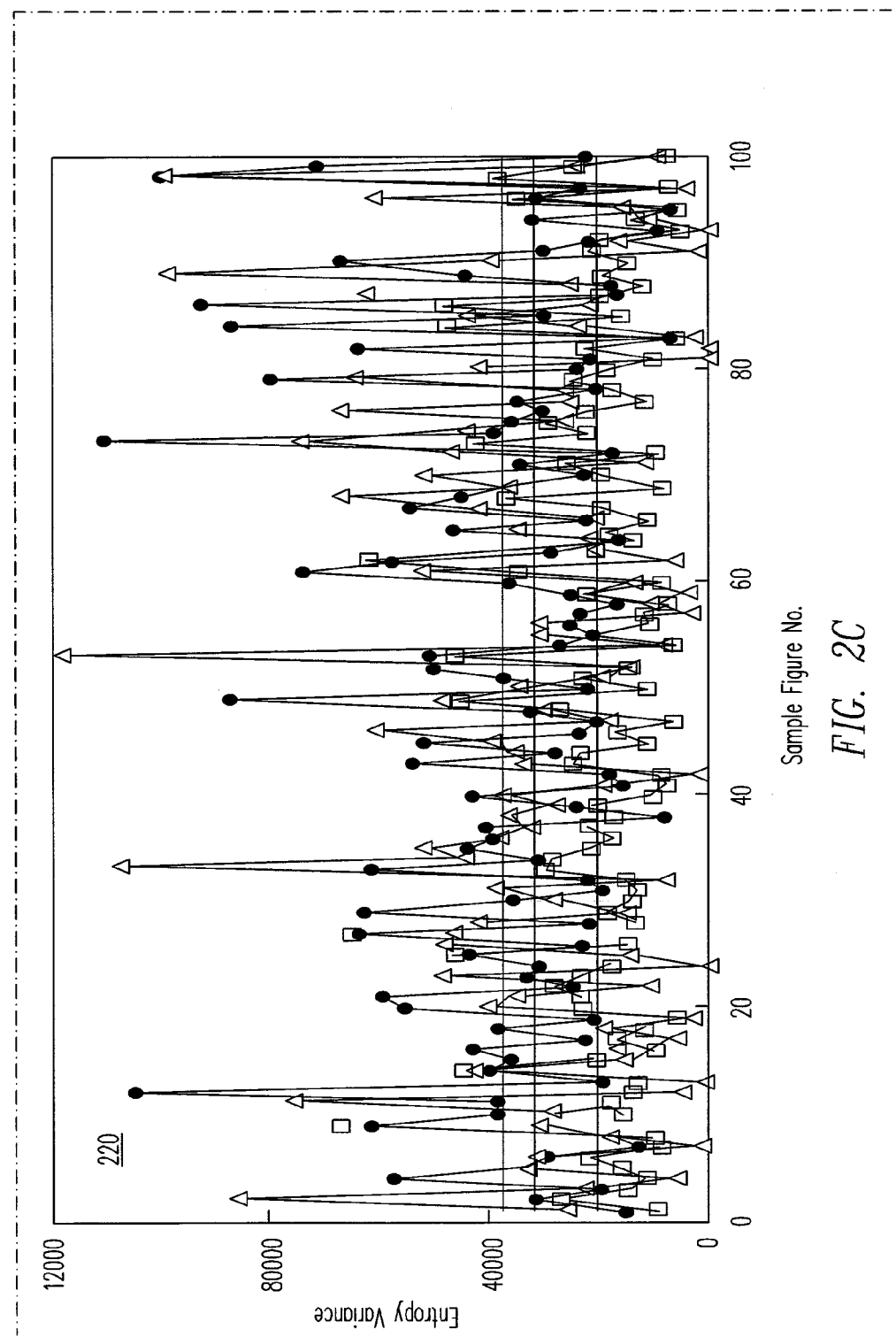
FIG. 2C. Shows the processing of the images using an entropy variance calculation according to some embodiments of the present invention.

FIGS. 2A-2D show the processing of image frames using an entropy variance calculation and an auto-correlation calculation, according to some embodiments of the present invention. The entropy variance calculation is obtained using Eq. (8) and the results are shown in graphs 220 and 225 of FIGS. 2C and 2D. The auto-correlation calculation according to the embodiments depicted in FIGS. 2A and 2B is obtained by first providing an image matrix and then obtaining a one dimensional image vector from aligning each of the rows in the image matrix along a single sequence (cf. FIG. 1B). In some embodiments of the present invention, the image matrix may be a two-dimensional array of values where each value is the digital count or intensity associated to a corresponding sector of the image that has been divided accordingly. An auto-correlation Y obtained from a one-dimensional vector X having N components is defined by the following mathematical expression:

$$Y_j = \sum_{k=0}^{N-1} X_k^* \cdot X_{j+k} \quad (9)$$

Where the index j is an integer number that may vary from $j=-(N-1)$, to $j=N-1$, including $j=0$. Thus, according to some embodiments of the invention as depicted in FIG. 2, the auto-correlation vector of a one-dimensional vector, X, having N components results in a one-dimensional vector, Y, having 2N-1 components.

Once an auto-correlation vector is obtained from a first image vector, the operation according to graphs 210 in FIGS. 2A and 215 in FIG. 2B includes the finding of peaks and valleys in the trace of the auto-correlation vector Y (cf. Eq. (9)). Adding the values of the peaks and subtracting the values of the valleys in the trace of the auto-correlation vector Y a value is obtained for each image. The plots of values for a number of sample images are shown in graphs 210 (FIG. 2A) and 215 (FIG. 2B). Further details as to the forming of the auto-correlation vector Y will be described in detail in relation to FIGS. 3A-C below.

The results in FIGS. 2A-2D show that the values obtained by an entropy variance and by an auto-correlation do indeed provide discrimination between different figures in an image, such as triangles, circles and squares. Furthermore, the discrimination is more pronounced with an increase in the number of sectors into which the input image is divided.

Equation (8) illustrates how a reduction in the dimensionality of the data, originally composed of 200 pixels, can be performed in order to accomplish a simple task such as the discrimination between the shape of a circle, a triangle, and a square. However, in order to make use of dPCA, a linear operation is preferred, according to some embodiments of the present invention.

Figure 3A:
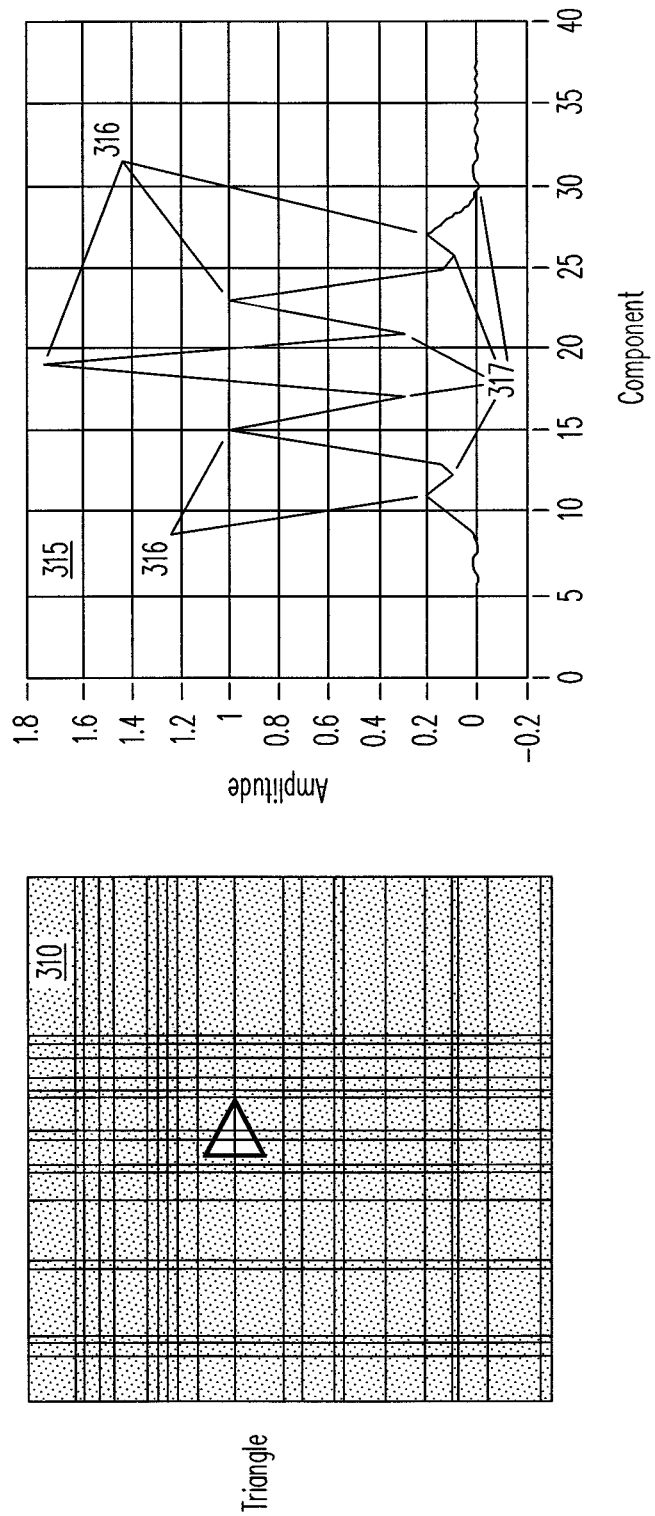
FIG. 3A. Shows a trace of an auto-correlation of an image vector according to some exemplary embodiments of the present invention, using a triangle.
Figure 3B:
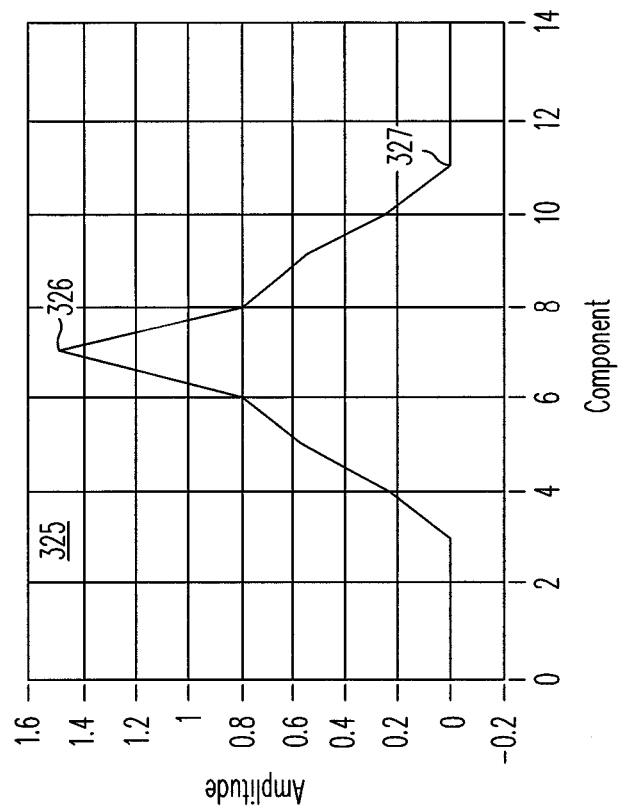
FIG. 3B. Shows a trace of an auto-correlation of an image vector according to some exemplary embodiments of the present invention, using a circle.
Figure 3B:
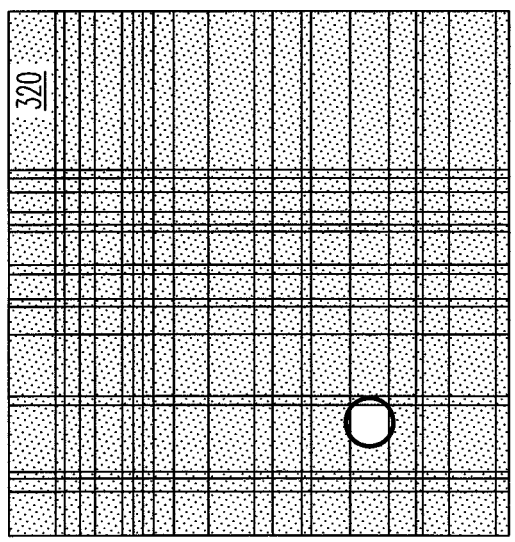

FIGS. 3A-3C show a set of traces obtained using an auto-correlation operation according to some exemplary embodiments of the present invention. In FIGS. 3A-3C the horizontal and vertical sectors selected for dividing an input image may not evenly divide the width and the height of the image. In some embodiments of the present invention, each of the sectors may have a different size relative to its neighboring sector, as shown in the sectors for a triangle 310 (cf. FIG. 3A), a circle 320 (cf. FIG. 3B), and a square 330 (cf. FIG. 3C). In fact, a random partition may be used in the horizontal and vertical direction to subdivide the image frame, according to the embodiments of FIG. 3A-3C. Further shown in FIGS. 3A-3C, some embodiments of the present invention may include the adding of the peaks and the subtraction of the valleys of an auto-correlation vector Y obtained using Eq. (9) from a first vector X obtained from the image as shown in FIG. 1B.

FIG. 3A shows an auto-correlation vector obtained from the sectors 310 of a triangle, leading to trace 315.

FIG. 3B shows an auto-correlation vector obtained from the sectors 320 of a circle leading to trace 325.

FIG. 3C shows an auto-correlation vector obtained from the sectors 330 of a square leading to trace 335.

In the exemplary embodiments depicted in FIGS. 3A-3C, the peak values of the auto-correlation vectors may be given by peaks 316 (triangle, FIG. 3A), 326 (circle, FIG. 3B), and 336 (square, FIG. 3C). The valley values may be given by values 317 (triangle, FIG. 3A), 327 (circle, FIG. 3B), and 337 (square, FIG. 3C).

Figure 4A:
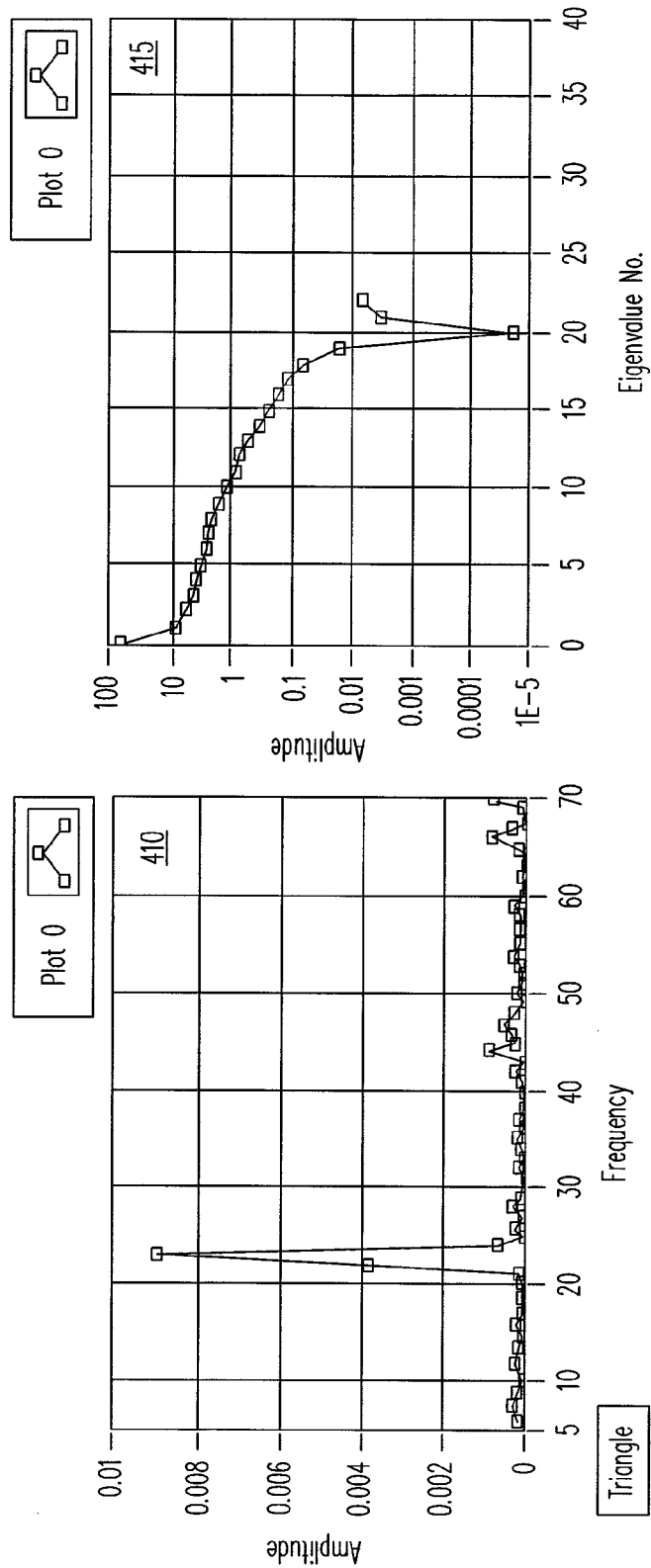
FIG. 4A. Shows the processing of the images using a power spectrum obtained with an (FFT) of an image vector and an eigenvalue calculation of an image matrix according to some embodiments of the present invention, using a triangle.
Figure 4B:
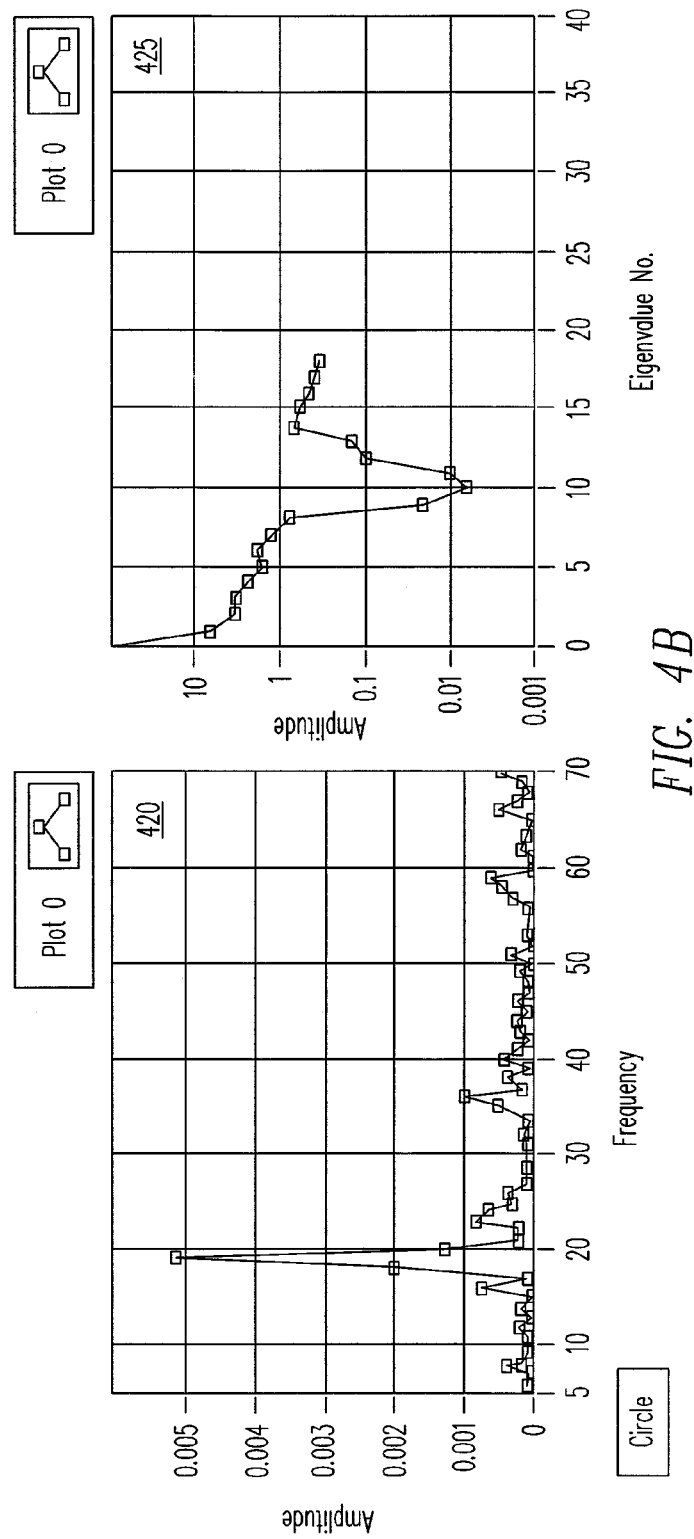
FIG. 4B. Shows the processing of the images using a power spectrum obtained with an (FFT) of an image vector and an eigenvalue calculation of an image matrix according to some embodiments of the present invention, using a circle.
Figures 4, 4C:
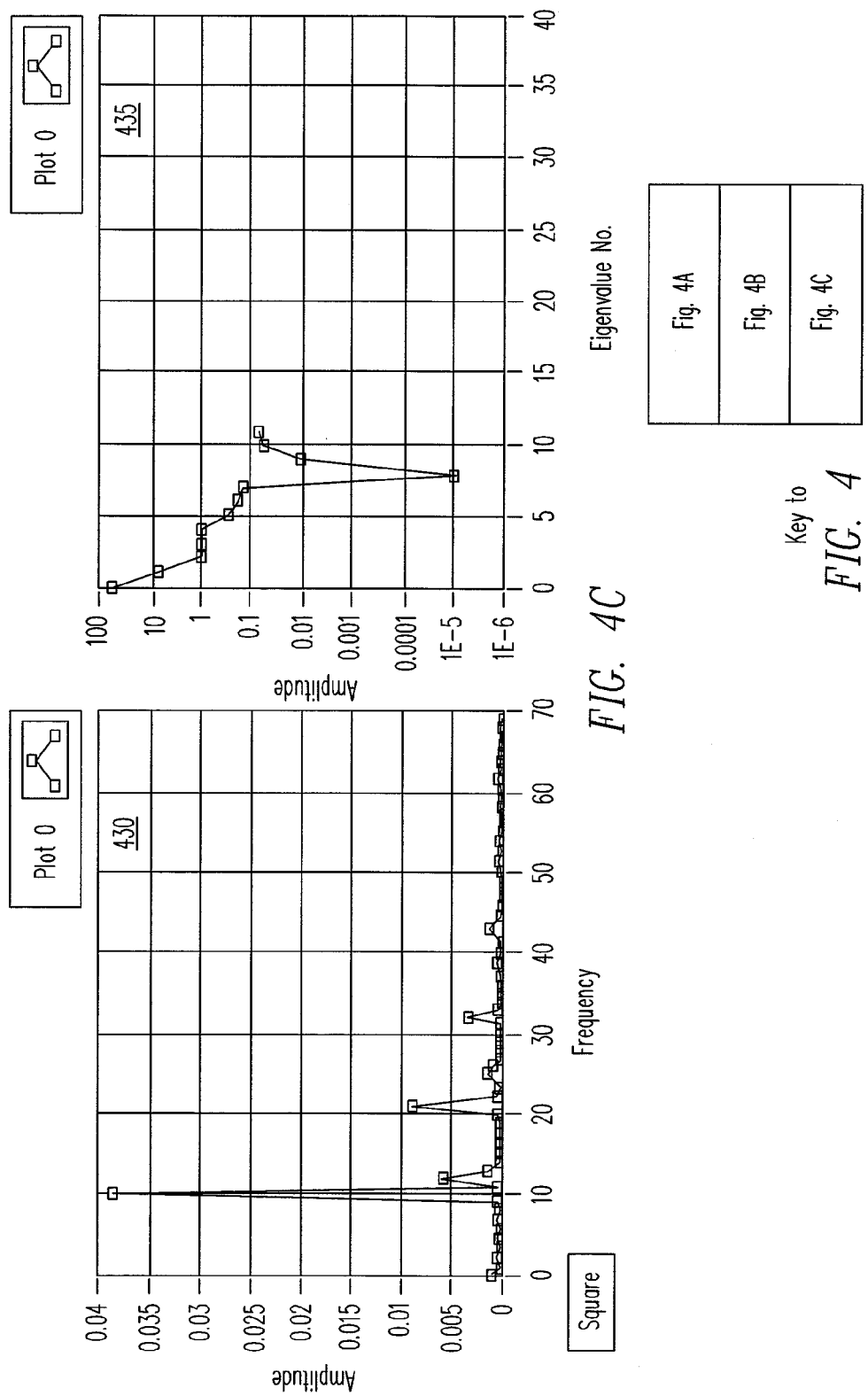
FIG. 4C. Shows the processing of the images using a power spectrum obtained with an (FFT) of an image vector and an eigenvalue calculation of an image matrix according to some embodiments of the present invention, using a square.

FIGS. 4A-4C show the processing of image frames using a power spectrum obtained with a Fast Fourier Transform calculation (FFT) and an eigenvalue decomposition, according to some embodiments of the present invention. The FFT transform is produced having as an input a vector X obtained from the image frame following the steps of FIG. 1B. The eigenvalues and eigenvectors are obtained from a u×v matrix formed by the digitalized values of the subdivided image frame (cf. FIG. 1B).

FIG. 4A shows a FFT power spectrum 410 from a triangle that gives rise to frequency peaks that have certain intensity and a frequency. FIG. 4A also shows an eigenvalue spectrum 415 obtained from the same triangle, having a maximum value and a minimum value.

FIG. 4B shows a FFT power spectrum 420 from a circle that gives rise to frequency peaks that have certain intensity and a frequency. FIG. 4B also shows an eigenvalue spectrum 425 obtained from the same circle, having a maximum value and a minimum value.

FIG. 4C shows a FFT power spectrum 430 from a square that gives rise to frequency peaks that have certain intensity and a frequency. FIG. 4C also shows an eigenvalue spectrum 435 obtained from the same square, having a maximum value and a minimum value.

According to FIGS. 4A-4C, the maximum frequency peak in the FFT 410 of a triangle has a higher intensity and is located at a higher frequency than the maximum frequency peak in an FFT power spectrum of a circle of the same area 420. The FFT power spectrum of a triangle 410 has a maximum peak with a lower intensity and higher frequency relative to the maximum peak in an FFT spectrum of a square of the same area 430. By the same token, triangular figures give rise to eigenvalues having an amplitude spectrum 415 that has a minimum value at a component positioned farther apart, relative to the minimum value encountered in an eigenvalue spectrum 425 of a circle of the same area, or the minimum valley in an eigenvalue spectrum 435 of a square of the same area.

Figure 5A:
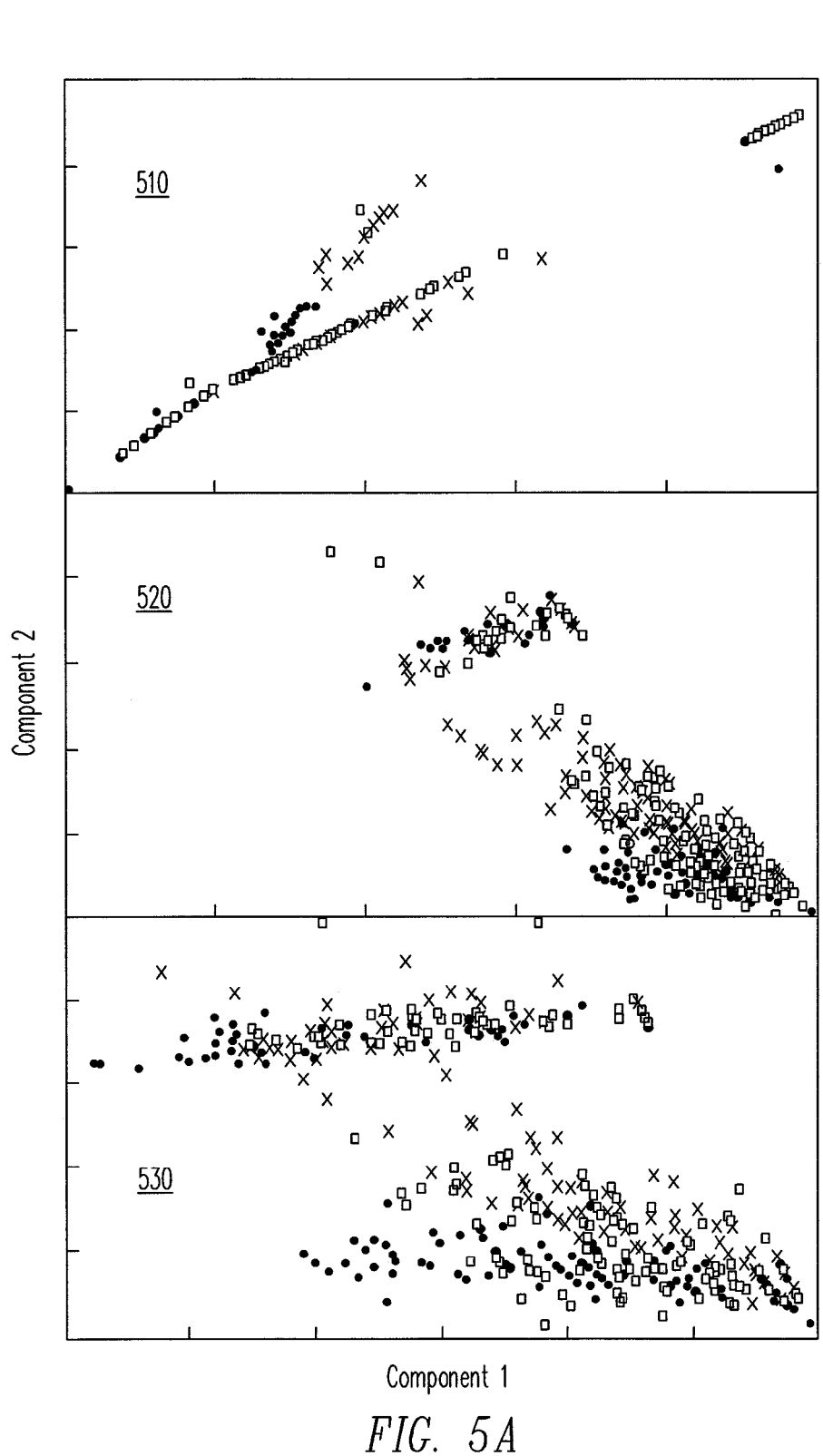
FIGS. 5A and 5B. Show a set of two-dimensional plots with a first component and a second component to distinguish between different geometric figures according to some embodiments of the present invention.
Figure 5B:
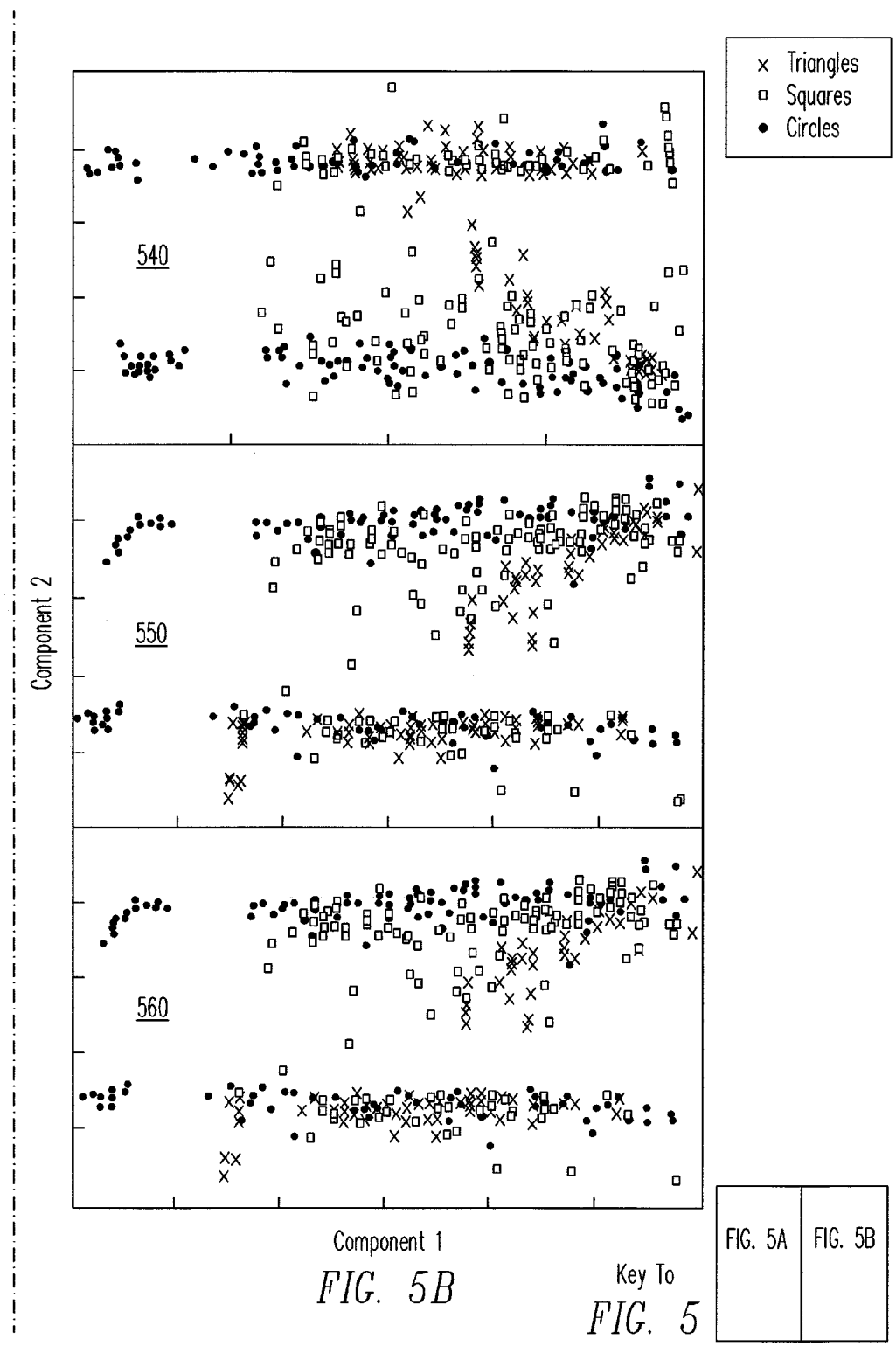

FIGS. 5A and 5B show a set of plots separating different figures using two-dimensional plots with a first component and a second component of a test vector selected for each sample figure according to some embodiments of the present invention. The steps of forming a test vector for each sample figure will be described in detail with respect to FIG. 7, below. In FIGS. 5A and 5B, two thousand (2000) calibration figures where used for each of the geometric shapes: a triangle, a circle, and a square having a different size and orientation relative to the image plane. In the case of triangular shapes, the relative size of each of the sides of the triangle was also changed arbitrarily for the two thousand (2000) calibration figures. A set of pattern matrices was obtained with a first selected set of characteristics being the peak frequency component in a power spectrum obtained by a FFT of a calibration image vector, and a second set of characteristics being the minimum eigenvalue in the eigenvalue spectrum of the calibration image matrix. The steps of forming each pattern matrix are described in detail with reference to FIG. 7, below.

To obtain FIGS. 5A and 5B, the above procedure was repeated for 200 sets of two thousand (2000) calibration images. In each of the graphs shown in FIG. 5A, each image was divided into 10 horizontal sectors by 10 vertical sectors 510; 30 horizontal sectors by 30 vertical sectors 520; and 50 horizontal sectors by 50 vertical sectors 530. In each of the graphs shown in FIG. 5B, each image was divided into 100 horizontal sectors by 100 vertical sectors 540; 150 horizontal sectors by 150 vertical sectors 550; and 200 horizontal sectors by 200 vertical sectors 560. It should be understood that the embodiments of FIG. 5A and FIG. 5B are exemplary only, and other embodiments may include a set of calibration images having a different size. Further, the number of horizontal sectors may be different from the number of vertical sectors, and may have any integer value. Some embodiments of the present invention may include a set of calibration images having the same size.

Figure 6:
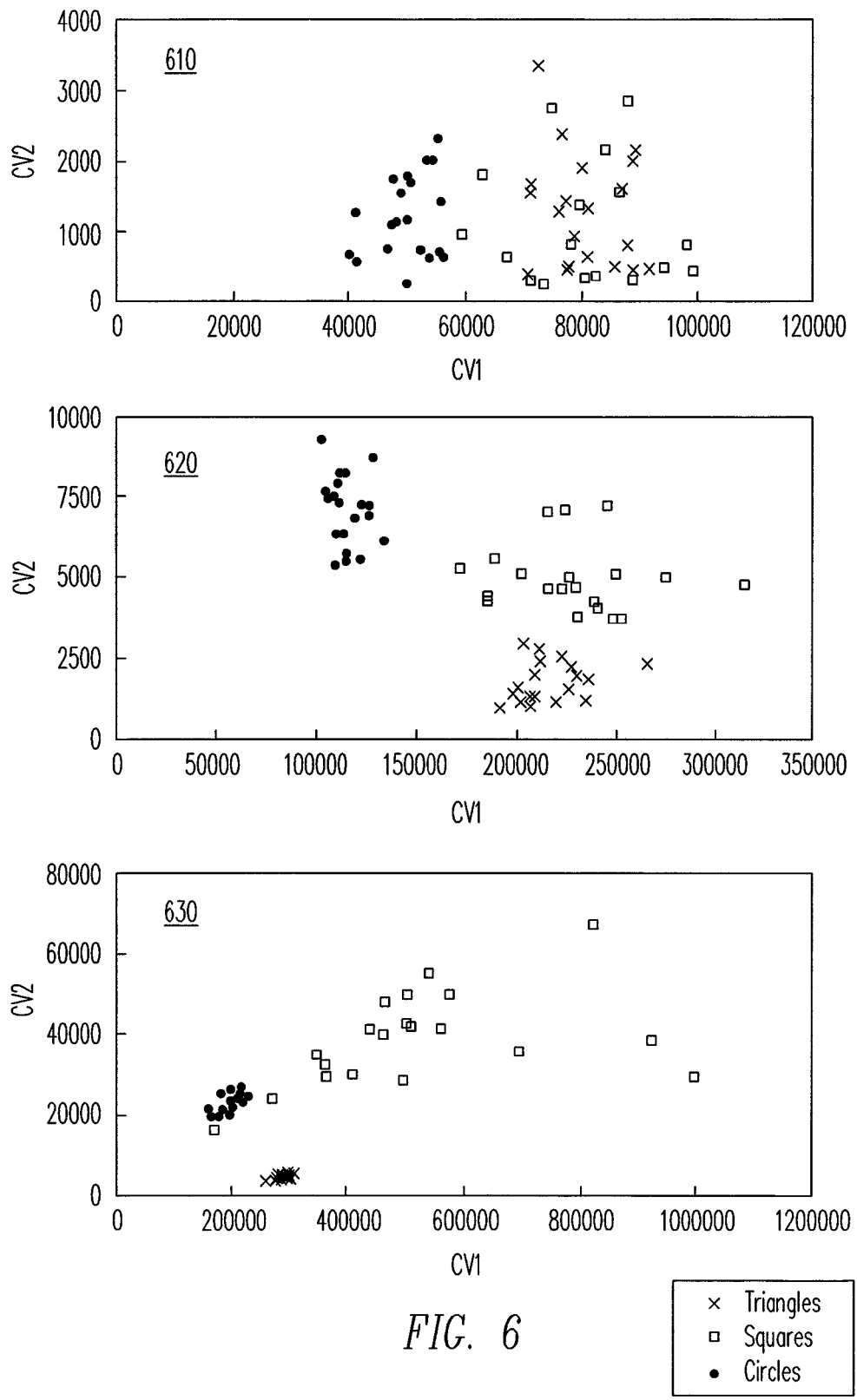
FIG. 6. Shows a set of two-dimensional plots corresponding to eigenvalues of matrices formed by selected vectors from sample figures and matrices formed by calibration figures according to some embodiments of the present invention.

FIG. 6. Shows a set of two-dimensional plots corresponding to the two-largest eigenvalues of pattern matrices formed by selected vectors from sample figures according to some embodiments of the present invention. The pattern matrices were obtained by dividing the image frame in 20 horizontal sectors by 20 vertical sectors 610, 50 horizontal sectors by 50 vertical sectors 620, and 150 horizontal sectors by 150 vertical sectors 630. The embodiments depicted in FIG. 6 are not limiting. It is understood that two-dimensional plots of eigenvalues from pattern matrices may be obtained by dividing image frames in a number of horizontal sectors that is substantially different from the number of vertical sectors.

Figure 7:
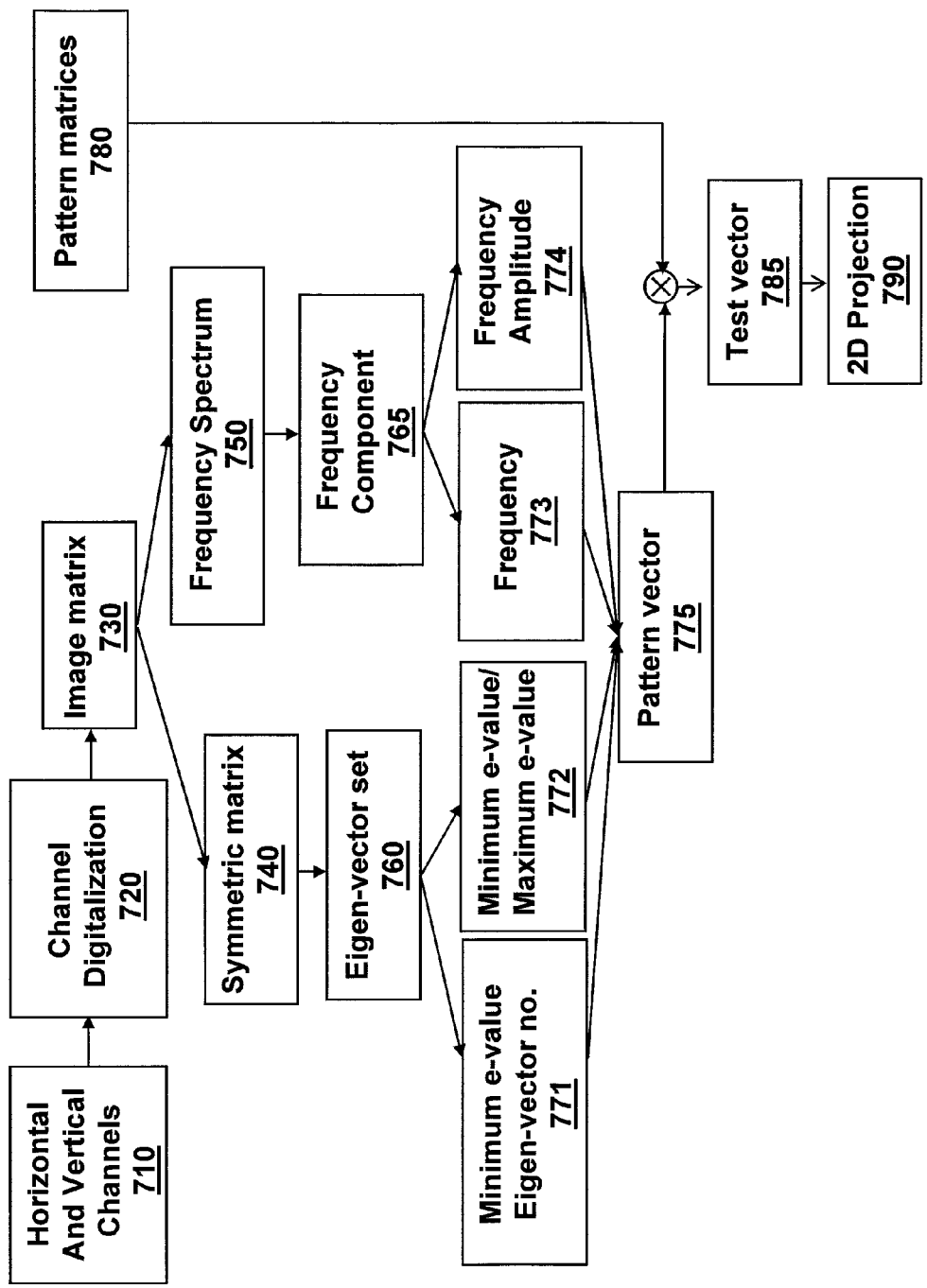
FIG. 7. Shows a flow diagram of a method for performing pattern recognition of figures and shapes provided by an optical device according to some embodiments of the present invention.

FIG. 7. Shows a flow diagram of a method for performing pattern recognition of figures and shapes provided by an optical device according to some embodiments of the present invention. The method includes the step of selecting a number of horizontal and vertical channels or sectors into which subdivide image frame 710. The image frame may be part of a set of calibration images or may be a sample image to be tested by the method disclosed herein. Once the number of channels or sectors has been selected, a channel digitalization step 720 assigns a numeric value to each of the channels or sectors into which the image has been subdivided. According to some embodiments of the present invention, the value assigned to each channel or sector is a digital value representing an average value of the intensity of the optical image in the given sector or channel. Other embodiments of the present invention may include a digital number representing the average value of the intensity of the optical image corresponding to a selected frequency or wavelength of light. In step 730 an image matrix is formed as a u×v matrix with the digitalized values of the subdivided image frame (cf. FIG. 1B). In some exemplary embodiments of the present invention, the image matrix may be such that along each of the rows of the matrix and along each of the columns of the matrix there is at least one value that is different from zero.

Step 750 takes the image matrix of step 730 as an input to provide a frequency spectrum from the image matrix. In some embodiments, the frequency spectrum is obtained from applying a FFT operation to a one-dimensional vector obtained by arranging rows in an image matrix obtained as in step 730 in a one-dimensional vector. The steps of forming a one-dimensional vector from an image matrix is illustrated in relation to FIG. 1B.

The frequency spectrum provided in step 750 is input to step 765, where a frequency component from said frequency spectrum is selected. According to some embodiments of the present invention, said frequency component is selected from the maximum amplitude shown in the frequency spectrum provided by step 750. Further, said frequency component selected from the frequency spectrum may comprise a frequency, obtained in step 773, and a frequency amplitude, obtained in step 774. In some embodiments of the present invention, said frequency may be a peak frequency in the frequency spectrum, and the frequency amplitude may be a peak frequency amplitude in the frequency spectrum.

Some embodiments of the present invention may also include step 740, in which a symmetric matrix is provided by using an image matrix from step 730 as an input. In some embodiments of the present invention, said symmetric matrix may be obtained by multiplying the mage matrix of step 730 by its own transpose. As one of ordinary skill in the art of linear algebra manipulation would know, the eigenvectors associated to a symmetric matrix may be formed as an orthogonal set of eigen-vectors. Furthermore, the set of eigenvalues associated to the eigenvectors from the symmetric matrix may have real values. The orthogonal set of eigenvectors of the symmetric matrix provided by step 740 is obtained in step 760, together with a set of eigenvalues. According to some embodiments of the present invention, said set of eigenvalues and eigenvectors is input to steps 771 and 772. In step 771, a first feature from the eigenvector set provided by step 760 is selected, and in step 772 a second feature from the eigenvector set provided by step 760 is selected. According to some embodiments of the present invention, the first feature selected in step 771 is the number of the eigenvector having the minimum eigenvalue according to step 760, and the second feature selected is a ratio between the minimum eigenvalue and the maximum eigenvalue in the set of eigenvalues provided by step 760.

Some embodiments of the present invention further include step 775 where the first feature from the eigenvector set provided by step 771, the second feature from the eigenvector set provided by step 772, the frequency provided by step 773, and the frequency amplitude provided by step 774 are input to form a pattern vector having four components. Other embodiments of the present invention may include a different number of features and components in the pattern vector formed in step 775. The pattern vector formed in step 775 is multiplied by a pattern matrix obtained according to step 780. The pattern matrix obtained according to step 780 is obtained by applying the same method as described above in steps 710-775 to obtain a set of pattern vectors for a collection of images included in a calibration set. Once a set of calibration pattern vectors is obtained according to the steps 710-775, said set of calibration pattern vectors is combined in step 780 as the rows in a matrix. This matrix is multiplied by its own transpose in step 780 to provide a pattern matrix. The pattern matrix thus obtained corresponds to a specific calibration set, and may be used to be multiplied to any other pattern vector formed from any sample image, according to steps 710-775. In any given pattern recognition problem, a pattern vector may be formed according to the steps 710-775 and then multiplied by each of the pattern matrices obtained according to step 780 to obtain a set of vectors. Test vector 785 is then selected having the maximum amplitude of the set of vectors resulting from multiplying the pattern matrices with the pattern vector. In some embodiments of the present invention, a characteristic pattern for the sample image is determined by the location of the projection of test vector 785 onto a two-dimensional plane, using the first two coordinates of the test vector.

In some embodiments of the present invention, once a set of calibration image matrices is obtained, an optimization procedure may be applied using a shell-cloud procedure as described in U.S. patent application Ser. No. 11/767,458, incorporated herein by reference in its entirety. A shell-cloud algorithm requires an L-dimensional parameter space, $Q^L$, where the optimization will take place, and a value to be maximized. In some embodiments of the present invention, the value to be maximized by a shell-cloud algorithm may be the distance between sets of points in a two-dimensional eigenvalue plot of pattern matrices, as described in FIG. 6. Each set of points representing a specific pattern class, will cluster around a mean value center. For example, in the embodiment depicted in FIG. 6, circles, triangles and squares are located in clusters separated from each other. The parameter space, $Q^L$, may include weight factors for the 16 components of the 4×4 pattern matrices formed according to the method described above, in relation to FIG. 7. Thus, a shell-cloud procedure may search for 16 weight factors to apply to each of the components in all the pattern matrices. The optimization procedure would maximize the distances between the mean value centers of the scattered plots corresponding to different pattern classes. In some embodiments, the shell-cloud algorithm may scan a 16-parameter space to maximize the area of a polygon described by the mean centers of the different pattern classes. The polygon may be a triangle, in the case of three figure classes, or a square in the case of four figure classes. Other types of polygons may be envisioned, depending on the number of different figure classes to be analyzed.

In other embodiments of the present invention, pattern matrices may have other dimensions, such as 2×2, or any other number. The parameter space to be scanned will have the dimension of the total number of components of the pattern matrices. In some embodiments, furthermore, the parameter space to be scanned may have a dimension that is smaller than the total number of components in the calibration image matrix. For example, if a given calibration image matrix is given by a 4×4 matrix H, then a new matrix G may be formed such that $$G_{ij} = \mu_i \cdot H_{ij}; \; i,j = 1,2,3,4 \qquad (10)$$

Where 'I' is an integer that may have a value from 1 to L=4×4=16, each value of 1 associated with one and only one coordinate '$H_{ij}$' of matrix H.

Figure 8:
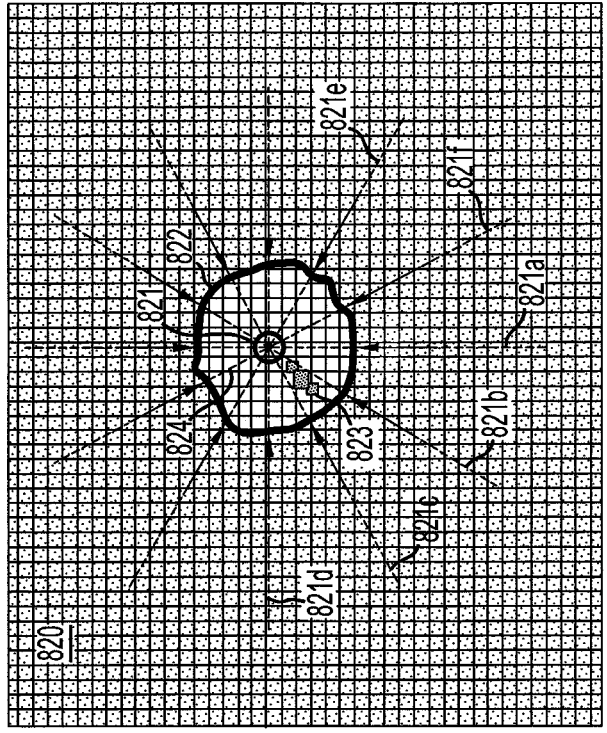
FIG. 8. Shows two images of a skin tissue sample where the ABCD technique is used to determine the presence of malignant melanoma according to some embodiments of the present invention.
Figure 8:
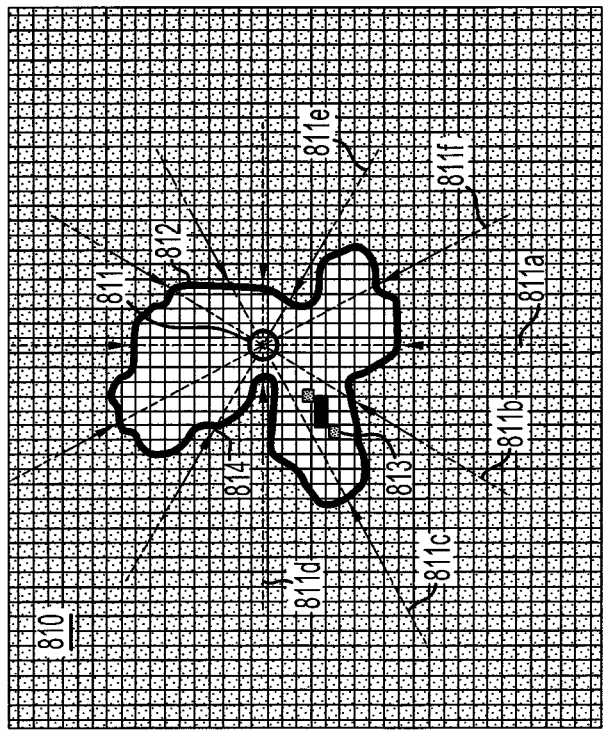

FIG. 8. Shows two images of a skin tissue sample where a pattern recognition technique such as described above in relation to FIGS. 1-7 is used to determine the presence of malignant melanoma, according to some embodiments of the present invention. For example, in FIG. 8 element 810 may be associated with a skin tissue showing a 'mole' or certain characteristic skin pattern. The 'mole' may have the features of asymmetry 811 (A), border 812 (B), color 813 (C), and diameter 814 (D), characteristic of malignant melanoma. This may be contrasted with element 820 showing a 'mole' having the features of asymmetry 821 (A), border 822(B), color 823 (C), and diameter 824 (D), characteristic of a normal 'mole' in the skin having no cancerous cells in it. According to the embodiment of the present invention depicted in FIG. 8, a pattern vector formed by the A, B, C, and D features from 810 and 820 may be formed, and multiplied to a pattern matrix formed by a process of calibration and training as described above, in relation to FIG. 7. By looking at the amplitude of the test vector, the tissue sample associated with the pattern vector may further be associated to a determined skin condition: either malignant melanoma, or normal tissue.

According to some embodiments of the present invention, as depicted in FIG. 8, elements 811 and 821 include a certain number of axes, 811a-811f, for element 810, and also 821a-821f, for element 820. Axes 811a-811f and 821a-821f define symmetry axes of the pattern 810 and 820, respectively. The set of symmetry axes used in both patterns 810 and 820 may be the same set of axes. In general, the symmetry axes used to obtain a pattern vector are the same as the symmetry axes used to obtain the pattern matrices from each image. It is observed that in the embodiment shown in FIG. 8, element 810 is highly asymmetric, relative to element 820. Furthermore, in some embodiments of the present invention, such as the one described in relation to FIG. 8, a numeric value for the asymmetry can be given by using the diameters of the object relative to each symmetry axes. The symmetry of the object 810 and 820 may be determined by evaluating the diameter of elements 810 and 820 along each of the symmetry axes. Then, rotating elements 811a-f and 821a-f clockwise such that each axis takes the place of the next one in a clockwise order, the diameters of elements 810 and 820 relative to the new axes are re-evaluated. For example, in the embodiment depicted in FIG. 8, it is seen that all the diameters associated with axes 821a-821f are similar; while the diameters associated with axes 811a-811f are all dissimilar.

For example, symmetry axes 811a-811f may be associated with the numbers 1-6, and a value $d_{ij}$ is given for the diameter associated to axis 'i' after it has been rotated to axis 'j'. Thus, a matrix, S, may be obtained as shown below, $$S = \begin{pmatrix} d_{11} & d_{12} & d_{13} \\ d_{21} & d_{22} & d_{23} \\ d_{31} & d_{32} & d_{33} \end{pmatrix} = \begin{pmatrix} d_{11} & d_{22} & d_{33} \\ d_{22} & d_{33} & d_{11} \\ d_{33} & d_{11} & d_{22} \end{pmatrix}, \quad (11)$$

If the axes in the figure are as 811a-f, and 822a-f, as depicted in FIG. 8, then a pattern such as 820 will have all columns in matrix S being the same, or very similar to each other, and the value of the determinant of matrix S will be close to zero. Moreover, the columns of matrix S in Eq. (11), resulting from a pattern such as 810 will be linearly independent. As shown in Eq. (11), the 3 column vectors in matrix S result from the permutation of three values that are different from one another. Therefore, according to some embodiments of the present invention, a measure of the asymmetry of a pattern such as 810 or 820 may be the determinant of matrix S.

One of regular skill in the art of pattern recognition would realize that in some embodiments of the present invention matrix S may be obtained by applying any symmetry operation to a set of symmetry axes. The symmetry operation may be defined as a geometric manipulation of a given image or pattern such that said image or pattern remains the same after said geometric manipulation. Furthermore, one of regular skill in the art may recognize that the choice of symmetry axes is arbitrary. According to some embodiments, the set of symmetry axes is chosen so that the determinant of the resulting matrix S for a pattern representing a normal tissue is zero or very close to zero.

FIG. 8 also shows the use of a border feature, depicted by elements 812 and 822 for objects 810 and 820, respectively. A border determination may include a measure of the length of the border 812 and 822 of objects 810 and 822, respectively. In some embodiments of the present invention, a value of the border length such as 812 and 822 may be normalized by a measure of the total area contained within border value 810 and 822. In some embodiments, the normalization of border lengths 812 and 822 may take place with respect to a maximum diameter of objects 810 and 820 along symmetry axes 811a-811f, and 821a-821f, respectively.

Another feature that may be used according to some embodiments of the present invention for the recognition of pathologic conditions may be the color contained in patterns 810 and 820. This is depicted in elements 813 and 823 of FIG. 8, respectively. In some cases, it may be observed that variability in pigmentation or color within the borders of the section under study, such as section 810 or 820, may be related to a malignant tissue condition, such as melanoma. A feature such as color or pigmentation of a given section of the tissue pattern under analysis, 813 or 823, may be obtained by an optical system using a suitable filter to select a predetermined portion of the wavelength spectrum of light to be collected from the image.

In some embodiments of the present invention, a diameter 814 or 824 of the 'mole' or tissue pattern 810 or 820 may be determined, as shown in FIG. 8. For example, in some embodiments, diameter 814 or 824 may be an average of the diameters associated with symmetry axes 811a-811f or 821a-821f. In other embodiments, the diameter feature may be the maximum or the minimum of diameters associated with symmetry axes 811a-811f, or it may be the median value of the diameters associated with the symmetry axes 811a-811f.

It is understood that different tissue conditions may be analyzed following the method described in accordance to FIG. 8. For example, some embodiments of the present invention may include images of skin samples presenting malignant melanoma, seborrhoeic keratosis, pigmented nevi, basal cell carcinoma, or squamous cell carcinoma. Thus, according to some embodiments of the present invention, a calibration set of tissue images corresponding to each of the previously mentioned skin conditions may be obtained, and a set of pattern matrices corresponding to each of the skin tissue conditions may be formed. A sample pattern vector may be formed from a sample tissue image following the same steps as described in relation to FIG. 7 and FIG. 8. The sample pattern vector may be multiplied with each of the calibration pattern matrices to find out which operation produces the vector having maximum amplitude. The vector having maximum amplitude is then projected on a two-dimensional plane, and the location of the projection on the plane may indicate the particular skin condition to which the sample skin tissue belongs.

In some embodiments of the present invention a shell-cloud procedure may be used with the calibration tissue image matrices described above, as in Eq. (10). The shell-cloud procedure finds values of a parameter vector having L components, such that a value is maximized. In some embodiments of the present invention, the value to be maximized may be the distance between mean centers in a 2-dimensional plot of eigenvalues of the calibration pattern matrices. The mean centers in the eigenvalue plot corresponding to a set of points obtained from pattern matrices grouped by the type of tissue condition that is under analysis. According to some embodiments of the present invention, each of the L components in the parameter vector that is sought by the shell-cloud procedure multiplies one component in a calibration tissue image matrix. Note that the calibration tissue image matrix may be the digitalized matrix of dimensions u×v obtained according to some embodiments depicted in FIG. 1B. According to yet some other embodiments of the present invention, each of the L-components in the parameter vector sought by the shell-cloud procedure multiplies one component in a pattern matrix obtained from a calibration image sample.

Furthermore, some embodiments of the present invention may use a shell-cloud procedure to scan a $Q^L$ parameter space looking to maximize the difference between the determinants of a symmetry matrix S obtained for different calibration tissue samples. In this case, the dimension L of the parameter space is given by the number of components in symmetry matrices S. As was discussed above in relation to Eq. (11), the dimension of symmetry matrix S is given by the choice of a set of symmetry axes. In some embodiments of the present invention, the symmetry axes used for all calibration tissue samples are the same.

Some embodiments of the present invention include an algorithm that enables the well-known technique of Principal Component Analysis to be utilized in a fast and cost-effective manner. By doing this, the Discrete Principal Component Analysis (dPCA) algorithm and structures used in connection with the method disclosed herein, allows the use and application of PCA techniques in sensing and imaging devices that can perform real time operations and multiple component identification. This optimization technique applies equally to the measurement of other materials (i.e. principal components) in other mixtures. Some embodiments of this invention make possible the measurement of principal components in mixtures using a minimum number of measurement channels without losing quality of performance, thus significantly lowering the cost and decreasing the time required to make the measurements compared to prior measurement techniques.

Other embodiments of the methods and techniques described in this disclosure may be obvious to one of regular skill in the art of pattern recognition, digital image processing, or histology analysis. The foregoing disclosure is only descriptive and not limiting of the embodiments contained within the following claims.

What is claimed is:

1. A method for associating a characteristic pattern to an image frame provided by an optical device, said method comprising:
    selecting a calibration set of images having characteristic figures with a pattern recognition system;
    dividing the image frame in a number of horizontal and vertical channels with the pattern recognition system;
    obtaining a digital signature for the image frame corresponding to each channel to create a calibration image matrix;
    obtaining a first set of characteristics and a second set of characteristics from said calibration image matrix;
    selecting two coordinates from at least one component in each of said first and second sets of characteristics from said calibration image matrix;
    forming a pattern vector from said selected coordinates from at least one component in each of said first and second sets of characteristics from said calibration image matrix;
    forming a calibration pattern matrix using pattern vectors from a plurality of said calibration images;
    forming a sample pattern vector from said selected coordinates from at least one component in each of said first and second sets of characteristics from a sample image;
    selecting a test vector from a set of vectors obtained by multiplying a sample pattern vector by each of the calibration image matrices;
    determining whether the image frame corresponds to a calibration pattern by the location in a two-dimensional plot of a two-dimensional projection of said test vector; and
    associating a characteristic pattern to the image frame based on the determined calibration pattern with the pattern recognition system.

2. The method of claim 1 wherein forming a calibration pattern matrix using pattern vectors comprises forming a first matrix by arranging the pattern vectors as the rows of the first matrix and multiplying the first matrix with a second matrix resulting from transposing the first matrix.

3. The method of claim 1 wherein selecting the test vector comprises selecting the vector having the largest magnitude of the set of vectors resulting from multiplying said pattern vector with each of said calibration pattern matrices.

4. The method of claim 1 wherein selecting the number of horizontal and vertical channels comprises minimizing the information entropy variance of the resulting calibration image matrix.

5. The method of claim 1 wherein obtaining said first set of characteristics comprises obtaining an auto-correlation vector from said calibration image matrix, and obtaining said second set of characteristics comprises obtaining an entropy variance from said calibration image matrix.

6. The method of claim 1 wherein obtaining said first set of characteristics comprises obtaining a frequency spectrum from the calibration image matrix, and obtaining said second set of characteristics comprises obtaining an eigenvalue spectrum from the calibration image matrix.

7. The method of claim 6 wherein said selected coordinates from at least one component in each of said first and second sets of characteristics comprise an amplitude and a frequency from said frequency spectrum, and further comprise an eigenvalue number and an eigenvalue ratio from said eigenvalue spectrum; and further wherein
    forming said pattern vector comprises selecting said amplitude and frequency from said frequency spectrum and said eigenvalue number and eigenvalue ratio from said eigenvalue spectrum.

8. The method of claim 7 wherein selecting an amplitude and a frequency from said frequency spectrum comprises selecting the maximum amplitude in the spectrum and the frequency at which the maximum occurs in the spectrum.

9. The method of claim 7 wherein said eigenvalue number is the number of the eigenvector having the minimum eigenvalue from said eigenvalue spectrum, and the eigenvalue ratio is a ratio between the minimum eigenvalue and the maximum eigenvalue in said eigenvalue spectrum.

10. The method of claim 6 wherein obtaining a frequency spectrum comprises:
forming a vector by arranging the elements of the image matrix in one dimension; and
performing a Fast-Fourier Transform of said vector.

11. The method of claim 6 wherein forming said eigenvalue spectrum comprises obtaining a set of eigenvectors and eigenvalues of said pattern matrix.

12. The method of claim 1 further comprising the step of using a shell-cloud procedure to scan a parameter space that maximizes the distance between the mean centers of the calibration pattern matrix eigenvalues projections, and further providing new calibration pattern matrices by selecting a set of parameters according to said shell-cloud procedure.

13. The method of claim 1 wherein the image frame comprises spectroscopic data of a sample comprising at least one of the group consisting of Raman spectra, fluorescence spectra, and infrared absorbance and reflectance spectra.

14. The method of claim 1 wherein associating a characteristic pattern includes a geometric property of an object in the image frame.

15. A method for recognizing tissue conditions in a sample tissue image frame provided by an optical device, said method comprising:
selecting a calibration set of tissue images having characteristic tissue conditions with a pattern recognition system;
selecting a number of horizontal and vertical channels for dividing the tissue image with a pattern recognition system;
obtaining a digital signature for the tissue image corresponding to each channel to create a calibration tissue image matrix;
obtaining a first set of characteristics and a second set of characteristics from said calibration tissue image matrix;
selecting two coordinates from at least one component in each of said first and second sets of characteristics from said calibration tissue image matrix;
forming a pattern vector from said selected coordinates from at least one component in each of said first and second sets of characteristics from said calibration tissue image matrix;
forming a calibration pattern matrix using pattern vectors from a plurality of said calibration tissue images;
forming a sample pattern vector from said selected coordinates from at least one component in each of said first and second sets of characteristics from a sample tissue image obtained from a sample tissue;
obtaining a two-dimensional projection of the vector resulting from transforming a sample pattern vector by the calibration pattern matrix;
determining with the pattern recognition system whether the sample tissue corresponds to a characteristic tissue condition in the calibration tissue pattern by the location in a two-dimensional plot of said projection.

16. The method as in claim 15 further wherein:
selecting a calibration set of tissue images comprises selecting images of skin tissue from different human samples, said tissue having different conditions comprising malignant melanoma, pigmented nevi, basal cell carcinoma, squamous cell carcinoma, and normal skin.

17. The method as in claim 15 further wherein:
obtaining a first set of characteristics and a second set of characteristics comprises obtaining an asymmetry value, a border value, a color value, and a diameter value.

18. The method as in claim 17 further wherein:
obtaining an asymmetry feature value comprises
selecting a set of symmetry axes and assigning a diameter for each symmetry axis;
transforming the symmetry axes according to a set of symmetry operations;
forming a matrix using the diameters assigned for the symmetry axes as they are transformed by the symmetry operations;
obtaining the determinant of said matrix.

19. The method of claim 18 further comprising the step of using a shell-cloud procedure to scan a parameter space that maximizes the difference in said determinants of said matrices, wherein each matrix is associated with a selected tissue condition, and further providing new matrices by selecting a set of parameters according to said shell-cloud procedure.

20. The method of claim 15 further comprising the step of using a shell-cloud procedure to scan a parameter space that maximizes the distance between the mean centers of the calibration tissue image matrix eigenvalues projections, and further providing new calibration tissue image matrices by selecting a set of parameters according to said shell-cloud procedure.

* * * * *